United States Patent
Hansen et al.

(10) Patent No.: US 12,070,399 B2
(45) Date of Patent: Aug. 27, 2024

(54) PROSTHETIC ANKLE ASSEMBLY AND ANKLE-FOOT SYSTEM COMPRISING SAME

(71) Applicant: United States Government as Represented by the Department of Veterans Affairs, Washington, DC (US)

(72) Inventors: Andrew Hansen, Minneapolis, MN (US); Gregory Owen Voss, Minneapolis, MN (US); Eric Nickel, Minneapolis, MN (US); Emily Hein, Minneapolis, MN (US)

(73) Assignee: United States Government As Represented By The Department Of Veterans Affairs, Washington, DC (US)

( * ) Notice: Subject to any disclaimer, the term of this patent is extended or adjusted under 35 U.S.C. 154(b) by 187 days.

(21) Appl. No.: 17/253,294

(22) PCT Filed: Jun. 17, 2019

(86) PCT No.: PCT/US2019/037513
§ 371 (c)(1),
(2) Date: Dec. 17, 2020

(87) PCT Pub. No.: WO2019/245981
PCT Pub. Date: Dec. 26, 2019

(65) Prior Publication Data
US 2021/0275329 A1    Sep. 9, 2021

Related U.S. Application Data

(60) Provisional application No. 62/686,268, filed on Jun. 18, 2018, provisional application No. 62/837,397, filed on Apr. 23, 2019.

(51) Int. Cl.
*A61F 2/66* (2006.01)

(52) U.S. Cl.
CPC .... *A61F 2/6607* (2013.01); *A61F 2002/6642* (2013.01); *A61F 2002/6671* (2013.01)

(58) Field of Classification Search
CPC ............ A61F 2/6607; A61F 2002/6642; A61F 2002/6671
See application file for complete search history.

(56) References Cited

U.S. PATENT DOCUMENTS

| 292,800 | A | * | 2/1884 | Furrer | A61F 2/6607 623/47 |
| 497,026 | A | * | 5/1893 | Judson | A61F 2/6607 623/47 |
| 4,718,913 | A | * | 1/1988 | Voisin | A61F 2/6607 623/49 |

(Continued)

FOREIGN PATENT DOCUMENTS

FR    2184210    11/1973

*Primary Examiner* — Jerrah Edwards
*Assistant Examiner* — Maximilian Tobias Spencer
(74) *Attorney, Agent, or Firm* — Ballard Spahr LLP

(57) ABSTRACT

Disclosed herein are devices, systems, and methods for accommodating quick and easy exchange of footwear for lower limb amputees. This abstract is intended as a scanning tool for purposes of searching in the particular art and is not intended to be limiting of the present invention.

37 Claims, 40 Drawing Sheets

(56) References Cited

U.S. PATENT DOCUMENTS

| | | | |
|---|---|---|---|
| 5,139,525 A | 8/1992 | Kristinsson | |
| 5,766,264 A * | 6/1998 | Lundt | A61F 2/6607 |
| | | | 623/47 |
| 6,099,572 A | 8/2000 | Mosler et al. | |
| 6,197,066 B1 | 3/2001 | Gabourie | |
| 2005/0137717 A1 | 6/2005 | Gramnas et al. | |
| 2008/0004718 A1 | 1/2008 | Mosler | |
| 2013/0173023 A1* | 7/2013 | Lecomte | A61F 2/4225 |
| | | | 623/55 |
| 2016/0100960 A1 | 4/2016 | Smith et al. | |
| 2017/0128236 A1 | 5/2017 | Meyer et al. | |
| 2018/0153712 A1* | 6/2018 | Albertsson | A61F 2/6607 |
| 2018/0289511 A1* | 10/2018 | Fairley | A61F 2/64 |

* cited by examiner

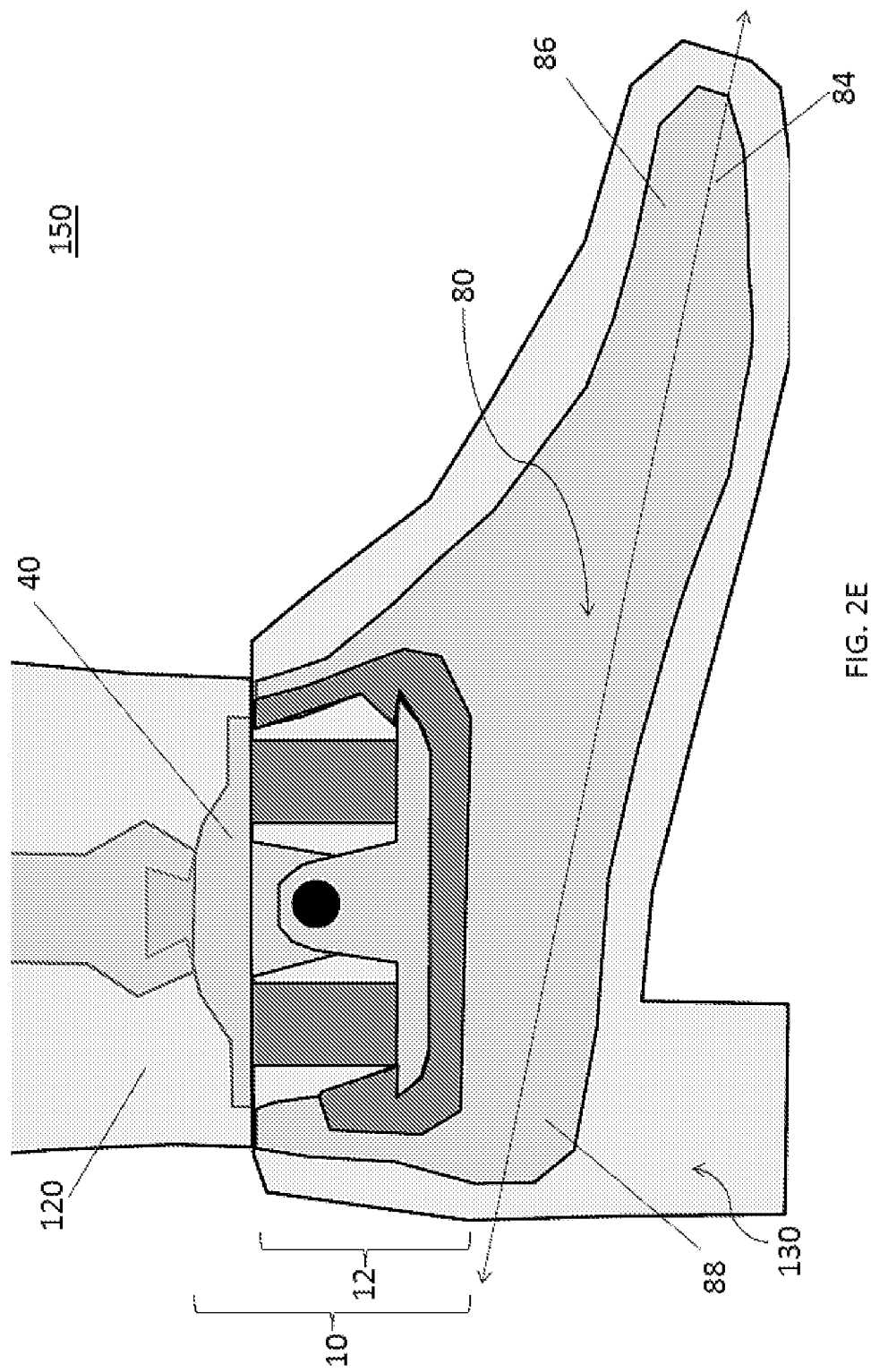

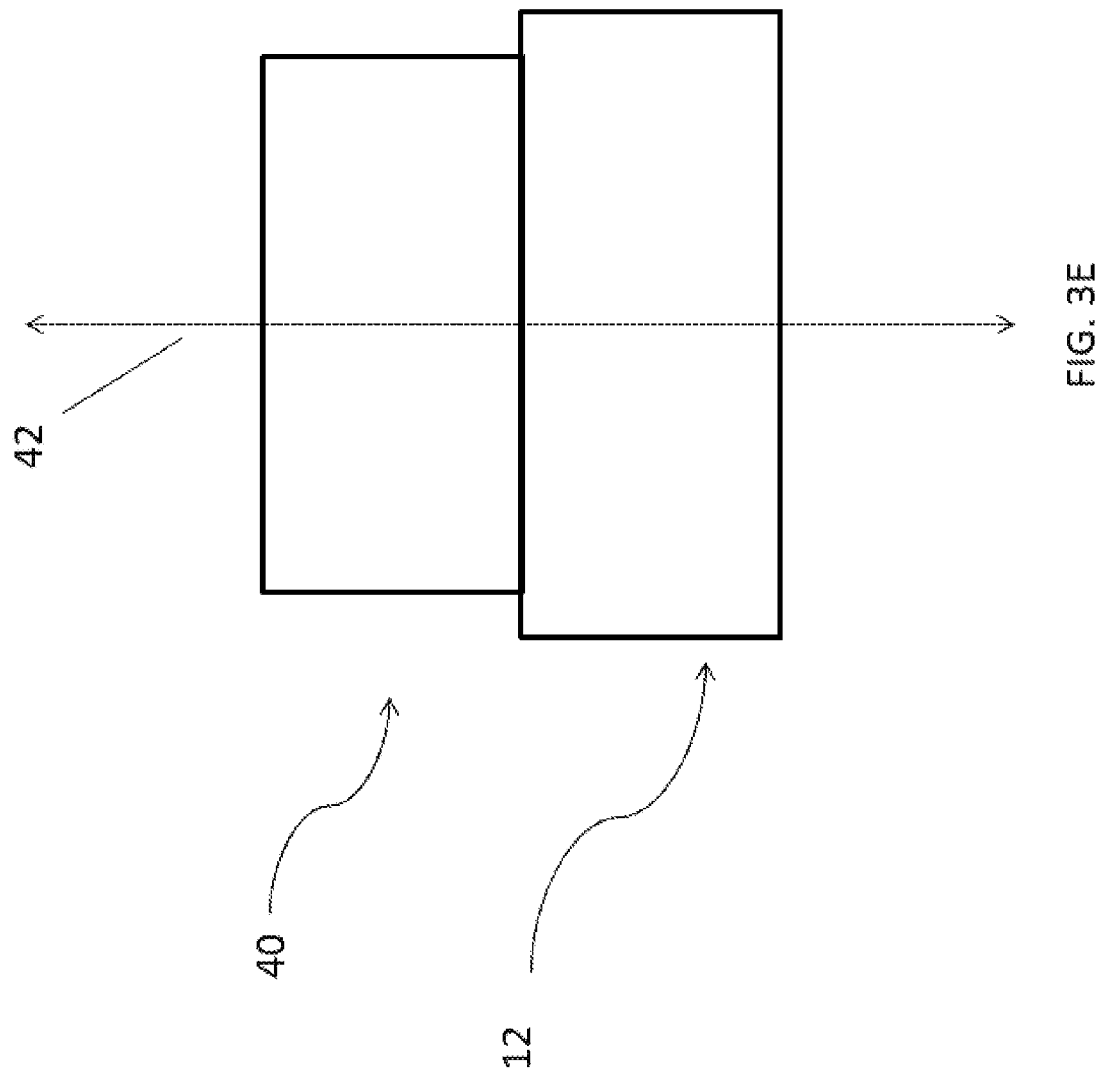

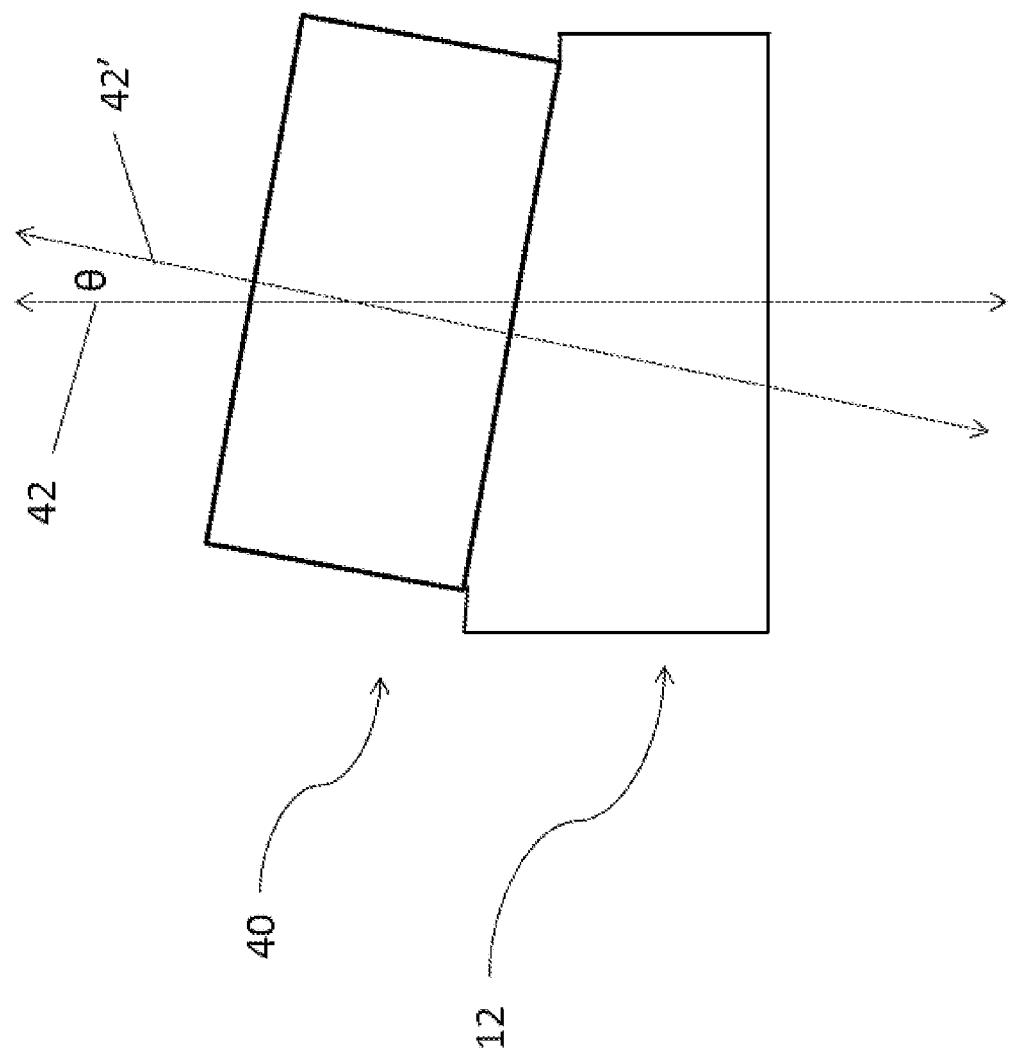

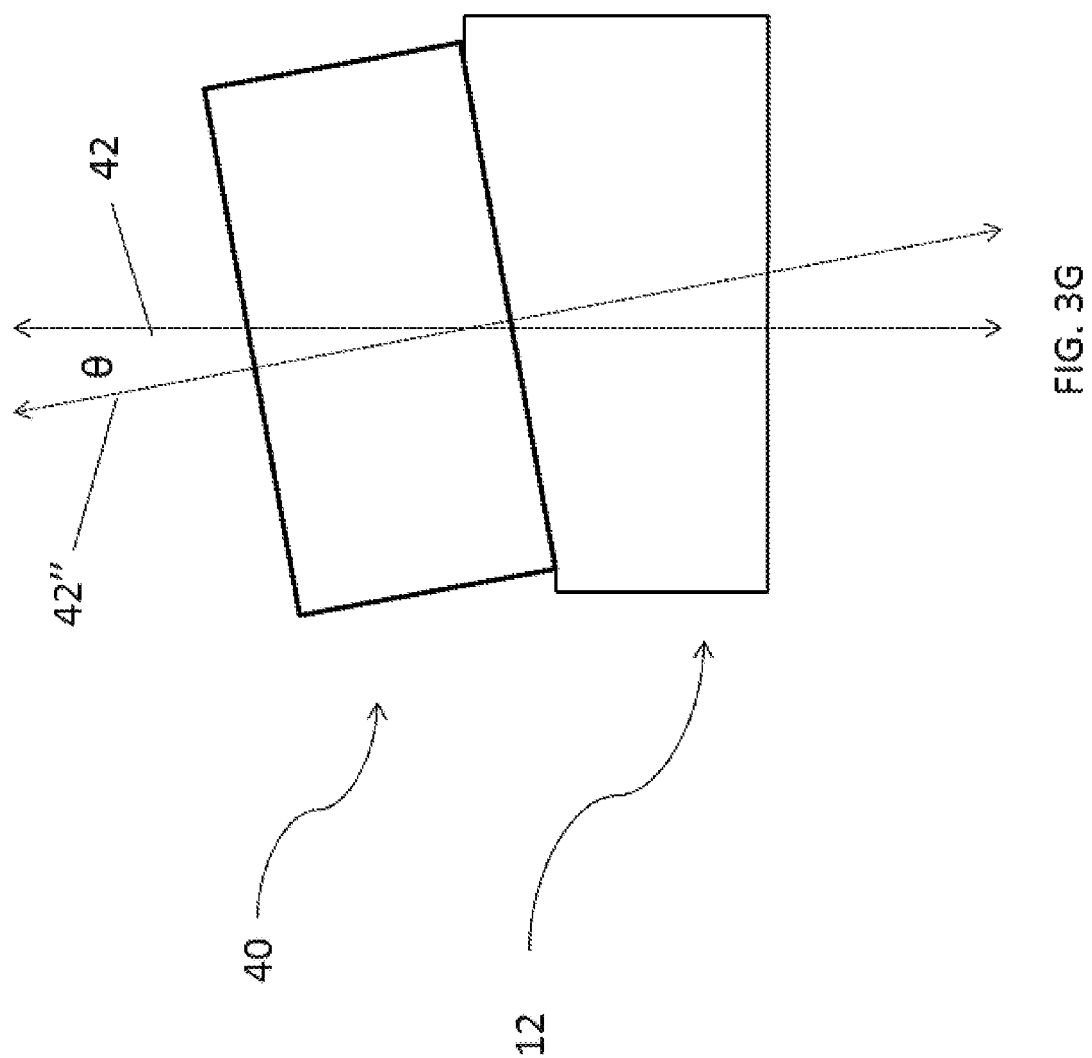

PROSTHETIC ANKLE ASSEMBLY AND ANKLE-FOOT SYSTEM COMPRISING SAME

CROSS REFERENCE TO RELATED APPLICATIONS

This is a U.S. National Phase Application of International Application No. PCT/US2019/037513, filed Jun. 17, 2019, which claims priority to and the benefit of the filing date of U.S. Provisional Application No. 62/686,268, filed Jun. 18, 2018, and U.S. Provisional Patent Application No. 62/837,397, filed Apr. 23, 2019. Both of these provisional applications are incorporated herein by reference in their entireties.

STATEMENT REGARDING FEDERALLY SPONSORED RESEARCH

This invention was made with government support from the Department of Veterans Affairs Rehabilitation Research and Development Service. The government has certain rights in the invention.

FIELD

This disclosure relates to ankle-foot prosthetic devices, and, more particularly, to ankle-foot prosthetic devices that allow quick and easy exchange of footwear having different heel heights.

BACKGROUND

The population of Veterans with amputations is steadily increasing, with the majority of these Veterans having lower-limb amputations. So, too, the female Veteran population is growing, with recent data indicating that over 2 million Veterans are women. The majority of commercially available prosthetic feet can only be used with shoes of a single heel height. Current heel-height adjustable prosthetic feet suffer from a range of disadvantages including that they can only be used within a narrow range of heel heights and require manual alignment changes by the user. Thus, there is a need for an easy-to-use, inexpensive, and lightweight prosthetic device for individuals with lower-limb amputations that is compatible with a variety of shoes of different heel heights.

SUMMARY

Disclosed herein, in various aspects, are ankle assemblies that comprise a resilient joint subassembly and an endoskeletal connector. The resilient joint subassembly can be configured for at least partial receipt within a receptacle defined by a prosthetic foot having a longitudinal axis and toe and heel portions spaced apart relative to the longitudinal axis. The endoskeletal connector can be secured to the resilient joint subassembly and configured for mechanical coupling with a prosthetic leg. Upon receipt of the resilient joint subassembly within the receptacle of the prosthetic foot, the resilient joint subassembly can be configured to permit pivotal movement of the endoskeletal connector from a start position relative to a transverse pivot axis that is perpendicular or oblique to the longitudinal axis of the prosthetic foot. Upon pivotal movement of the endoskeletal connector in a forward direction toward the toe portion of the prosthetic foot or in a rearward direction toward the heel portion of the prosthetic foot, the resilient joint subassembly can be configured to apply a return force to urge the endoskeletal connector toward the start position.

Also disclosed are foot-ankle systems that comprise a prosthetic foot and an ankle assembly. The prosthetic foot can define a receptacle and have a longitudinal axis and toe and heel portions spaced apart relative to the longitudinal axis. The ankle assembly can have a resilient joint subassembly and an endoskeletal connector. The resilient joint subassembly can be configured for at least partial receipt within the receptacle of the prosthetic foot. The endoskeletal connector can be secured to the resilient joint subassembly and configured for mechanical coupling with a prosthetic leg. Upon receipt of the resilient joint subassembly within the receptacle of the prosthetic foot, the resilient joint subassembly can be configured to permit pivotal movement of the endoskeletal connector from a start position relative to a transverse pivot axis that is perpendicular or oblique to the longitudinal axis of the prosthetic foot. Upon pivotal movement of the endoskeletal connector in a forward direction toward the toe portion of the prosthetic foot or in a rearward direction toward the heel portion of the prosthetic foot, the resilient joint subassembly can be configured to apply a return force to urge the endoskeletal connector toward the start position.

Also disclosed are methods comprising using a foot-ankle system as disclosed herein.

These and other features and advantages of the present invention will become more readily apparent when taken into consideration with the following description, the attached drawings, and the claims.

BRIEF DESCRIPTION OF THE DRAWINGS

FIG. 1A is a cross-sectional side view of an exemplary foot-ankle system as the ankle assembly is inserted within a receptacle of a prosthetic foot as disclosed herein. FIG. 1B is a cross-sectional side view of the foot-ankle system following receipt of the ankle assembly within the receptacle of the prosthetic foot as disclosed herein.

FIG. 2E is a cross-sectional side view of another exemplary foot-ankle system including the ankle assembly of FIG. 2A and the prosthetic foot of FIG. 2C.

FIGS. 3A-G are representative illustrations and images showing the movement of an ankle assembly with respect to an endoskeletal connector axis as disclosed herein. FIG. 3A depicts an exemplary endoskeletal connector in a resting/start position. FIG. 3B shows an image of an exemplary endoskeletal connector in the resting/starting position. FIG. 3C shows an image of the endoskeletal connector of FIG. 3B in a forward position. FIG. 3D shows an image of the endoskeletal connector of FIGS. 3B-C in a rear position.

FIG. 3E shows an isolated, schematic illustration of the endoskeletal connector (shown with a joint subassembly) in a resting/starting position. FIG. 3F shows a schematic illustration of the endoskeletal connector in a forward position at which the endoskeletal connector axis is oriented at a first angle relative to the endoskeletal connector axis in the resting/start position (θ>0°). FIG. 3G shows a schematic illustration of the endoskeletal connector in a rear position at which the endoskeletal connector axis is oriented at a second angle relative to the endoskeletal connector axis in the resting/start position (θ<0°).

FIG. 4A shows a plot of the mathematical relationship showing plantar insole shapes for eight different heel heights. FIG. 4B shows four representative keel designs developed using the mathematical relationship, as well as anatomical foot shapes. FIG. 4C shows a representative inexpensive prosthetic foot with roll-over shape overlaid on the image. FIG. 4D shows a representative heel design developed using the mathematical relationship, as well as the anatomical foot shape. FIG. 4E shows a representative keel design developed using the mathematical relationship. See Meier et al. (2014) J. Rehabil. Res. Dev., Development of inexpensive prosthetic feet for high-heeled shoes using simple shoe insole model. 51(3): 439-50.

FIG. 5A shows an ankle model to determine torsional stiffness values needed in a prosthetic ankle with a rigid keel to achieve the effective rocker shape radii for walking. FIG. 5B shows ankle torque versus ankle dorsiflexion angle plots for walking. The slope of the curve represents the torsional stiffness needed to provide biomimetic function for a prosthesis user weighing 1000 N.

FIG. 6A shows a representative bimodal ankle-foot system, which utilizes a rigid keel made of 3D-printed ULTEM™ plastic and a lockable ankle joint. FIG. 6B shows the walking roll-over shape (top line), which has a similar radius of curvature as the able-bodied ankle-foot system in walking, and the flatter effective shape of the system when the ankle is locked for standing or swaying (bottom line). See Hansen and Nickel (2013) *Journal of Medical Devices* 7(3): Article no. 035001.

FIG. 7A shows the ankle assembly secured to an endoskeletal connector as disclosed herein. FIG. 7B shows the ankle assembly prior to insertion into the receptacle of a prosthetic foot, which is already received within a shoe. FIG. 7C shows the ankle assembly partially inserted into the receptacle of the prosthetic foot. FIG. 7D shows the ankle assembly fully inserted into the receptacle of the prosthetic foot. FIG. 7E shows the ankle assembly being locked into the receptacle using a fastener as disclosed herein. FIG. 7F shows the ankle assembly as the fastener is fully advanced through the prosthetic foot to secure the joint subassembly within the receptacle of the prosthetic foot.

FIG. 8A shows an exemplary prosthetic foot outside of a shoe. FIG. 8B shows an exemplary prosthetic foot in a shoe having a low heel height, as conventionally known in the art. FIG. 8C shows an exemplary prosthetic foot in a shoe having a mid-range heel height, as conventionally known in the art. FIG. 8D shows an exemplary prosthetic foot in a shoe having a high heel height, as conventionally known in the art. It is contemplated that each prosthetic foot can have a different shape in order to permit complementary receipt within the various shoe designs. However, as further disclosed herein, it is contemplated that the same ankle assembly can be received within the receptacles of each differently-shaped prosthetic foot.

FIG. 9A shows an exemplary prosthetic foot in a shoe having a low heel height. FIG. 9B shows an exemplary prosthetic foot in a shoe having a mid-range heel height. FIG. 9C shows an exemplary prosthetic foot in a shoe having a high heel height.

DETAILED DESCRIPTION

Figure 1A:
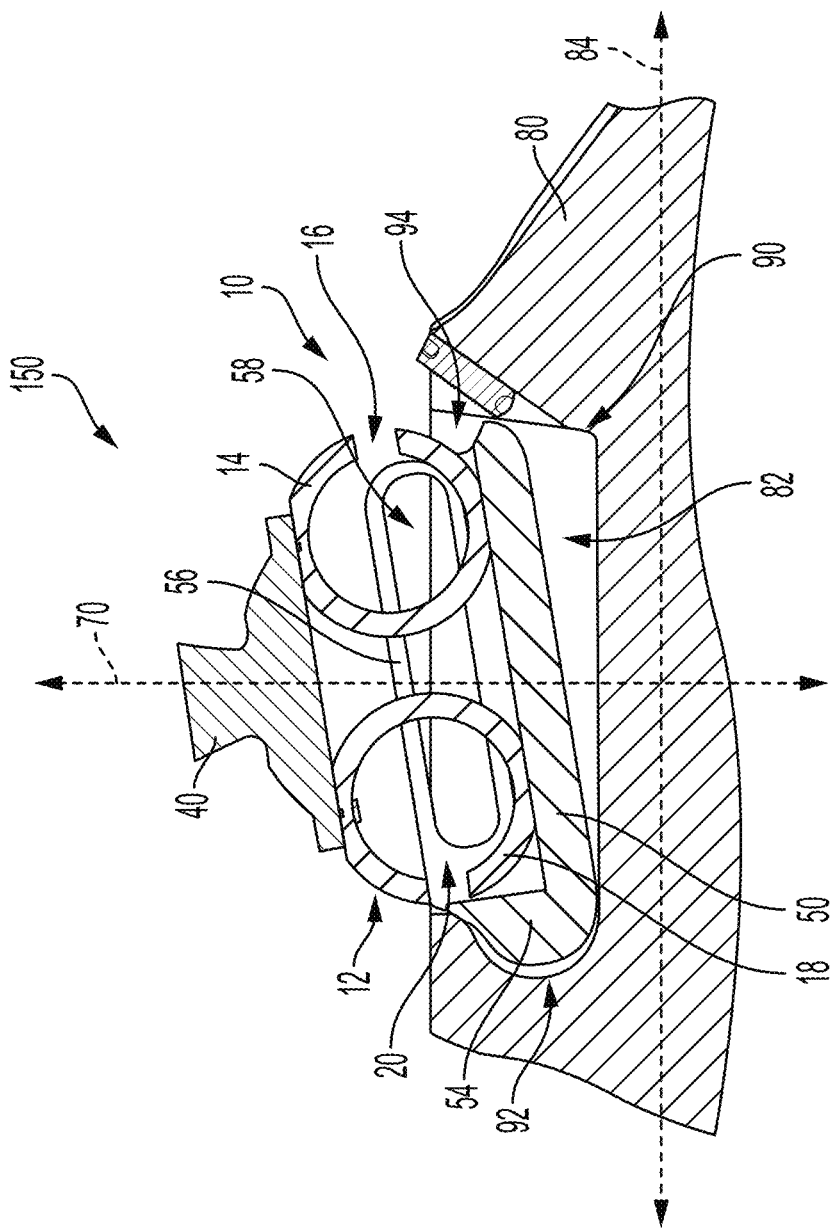
FIGS. 1A-B show exemplary foot-ankle systems comprising an ankle assembly having a resilient joint subassembly and an endoskeletal connector as disclosed herein.

The present disclosure can be understood more readily by reference to the following detailed description of the invention, the figures and the examples included herein.

The present invention now will be described more fully hereinafter with reference to the accompanying drawings, in which some, but not all embodiments of the invention are shown. Indeed, this invention may be embodied in many different forms and should not be construed as limited to the embodiments set forth herein; rather, these embodiments are provided so that this disclosure will satisfy applicable legal requirements. Like numbers refer to like elements throughout. It is to be understood that this invention is not limited to the particular methodology and protocols described, as such may vary. It is also to be understood that the terminology used herein is for the purpose of describing particular embodiments only, and is not intended to limit the scope of the present invention.

Many modifications and other embodiments of the invention set forth herein will come to mind to one skilled in the art to which the invention pertains having the benefit of the teachings presented in the foregoing description and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

Moreover, it is to be understood that unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is in no way intended that an order be inferred, in any respect. This holds for any possible non-express basis for interpretation, including matters of logic with respect to arrangement of steps or operational flow, plain meaning derived from grammatical organization or punctuation, and the number or type of aspects described in the specification.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided herein can be different from the actual publication dates, which can require independent confirmation.

DEFINITIONS

As used in the specification and the appended claims, the singular forms "a," "an" and "the" include plural referents unless the context clearly dictates otherwise.

The word "or," as used herein, means any one member of a particular list and also includes any combination of members of that list.

Throughout the description and claims of this specification, the word "comprise" and variations of the word, such as "comprising" and "comprises," means "including but not limited to," and is not intended to exclude, for example, other additives, components, integers, or steps. In particular, in methods stated as comprising one or more steps or operations it is specifically contemplated that each step comprises what is listed (unless that step includes a limiting term such as "consisting of"), meaning that each step is not intended to exclude, for example, other additives, components, integers, or steps that are not listed in the step.

Ranges can be expressed herein as from "about" or "approximately" one particular value, and/or to "about" or "approximately" another particular value. When such a range is expressed, a further aspect includes from the one particular value and/or to the other particular value. Similarly, when values are expressed as approximations, by use of the antecedent "about," or "approximately," it will be understood that the particular value forms a further aspect. It will be further understood that the endpoints of each of the ranges are significant both in relation to the other endpoint and independently of the other endpoint. It is also understood that there are a number of values disclosed herein and that each value is also herein disclosed as "about" that particular value in addition to the value itself. For example, if the value "10" is disclosed, then "about 10" is also disclosed. It is also understood that each unit between two particular units is also disclosed. For example, if 10 and 15 are disclosed, then 11, 12, 13, and 14 are also disclosed. Similarly, in some optional aspects, when values are approximated by use of the term "generally" or "substantially," it is contemplated that values within up to 15%, up to 10%, or up to 5% (above or below) of the particular value can be included within the scope of those aspects.

As used herein, the terms "optional" or "optionally" mean that the subsequently described event or circumstance may or may not occur and that the description includes instances where said event or circumstance occurs and instances where it does not.

INTRODUCTION

Disclosed herein, in various aspects, and with reference to FIGS. 1A-7D and 10A-10B, is a prosthetic device that can be quickly and easily connected to lightweight, inexpensive prosthetic feet that are designed to fit within shoes of different heel heights. The device is designed to provide biomimetic roll-over shape during walking and to permit changes from one shoe to the next with little or no alignment changes necessary by the prosthesis user.

Most commercially available prosthetic feet are designed for use with shoes of a fixed heel height. The prescribing clinician and the patient select an appropriate prosthetic foot and the fitting of the prosthesis is clinically optimized for the prosthetic foot-shoe combination. In these instances, deviation of shoe heel height should not occur after the prosthesis is aligned because it will negatively affect the gait of the user. Thus, once the prosthetic foot is aligned with a particular shoe, the patient is effectively limited to wearing a single shoe design, and, in contrast to the devices disclosed herein, there is no mechanism for freely and efficiently disconnecting the prosthetic leg of the patient to permit selective connection of the prosthetic leg with other (different) prosthetic foot/shoe combinations.

There are three ankle-foot systems currently on the prosthetics market that allow the user to change shoe heel heights between 0 to 2 inches. All heel height adjustable prosthetic ankle-foot systems have an ankle joint that allows a change in the sagittal plane alignment. A button can be pressed by the prosthesis user, allowing the ankle to rotate to a new angle, and then the button is pressed in the opposite direction to lock in the new alignment for shoes of different heel heights. The standard procedure is to have the prosthetist align the system with a particular pair of shoes and then educate the prosthesis user on how to change the alignment for shoes with different heel heights.

Current heel height adjustable ankle-foot prostheses can only accommodate a range of shoe heel heights between 0 and 2 inches, primarily because their plantar insole shape does not change with a change in the sagittal plane ankle alignment. Notably, most able-bodied women who wear high heels use heels much higher than 2 inches. Indeed, some able-bodied women wear high heels that are 5 inches or higher. Recently, an ankle with larger range of motion than current heel height adjustable ankle-foot prostheses was reported. However, the plantar insole surface of the feet does not adapt to match the insole shape of high heel footwear. This mismatch can cause instability, reduced durability of the foot and shoe, and is not cosmetically appealing.

Ankle Assemblies

Disclosed herein, in various aspects, and with reference to FIGS. 1A-3C, is an ankle assembly 10 configured to quickly and easily couple with a prosthetic foot 80, which can be produced using any conventional modeling technique. Optionally, it is contemplated that the prosthetic feet disclosed herein can be produced by a 3D-printer in accordance with a digital foot model as is known in the art.

Optionally, in various aspects, and with reference to FIGS. 1A-2E, the ankle assembly can comprise a resilient joint subassembly 12 and an endoskeletal connector 40. As used herein, "resilient joint subassembly" refers to a subassembly that is capable of returning to its initial shape after application of a first external force (e.g., an external bending, stretching, or compression force) without the need for application of a second external force that counteracts the first external force. As further described herein, it is contemplated that the disclosed resilient joint subassemblies can be configured to store and release energy within the ankle assembly. Optionally, as further disclosed herein, the resilient joint subassembly can comprise one or more springs or materials that exhibit spring-like properties such that the resilient joint subassembly quickly returns to its initial shape upon removal of the external force. In contrast to artificial joints that include electrical or mechanical actuators that are powered by an external power source, the mechanism by which the resilient joint subassembly returns to its initial shape is entirely self-contained so that application of external power is unnecessary. In these aspects, the resilient joint subassembly 12 can be configured for at least partial receipt within a receptacle 82 defined by a prosthetic foot 80 having a longitudinal axis 84. In an exemplary aspect, the endoskeletal connector 40 can be a pyramid connector as is known in the art, although alternative connectors as are known in the art are also envisioned. For example, an exoskeletal connector that takes an anatomical shape could instead be connected to the resilient joint subassembly.

Figure 1B:
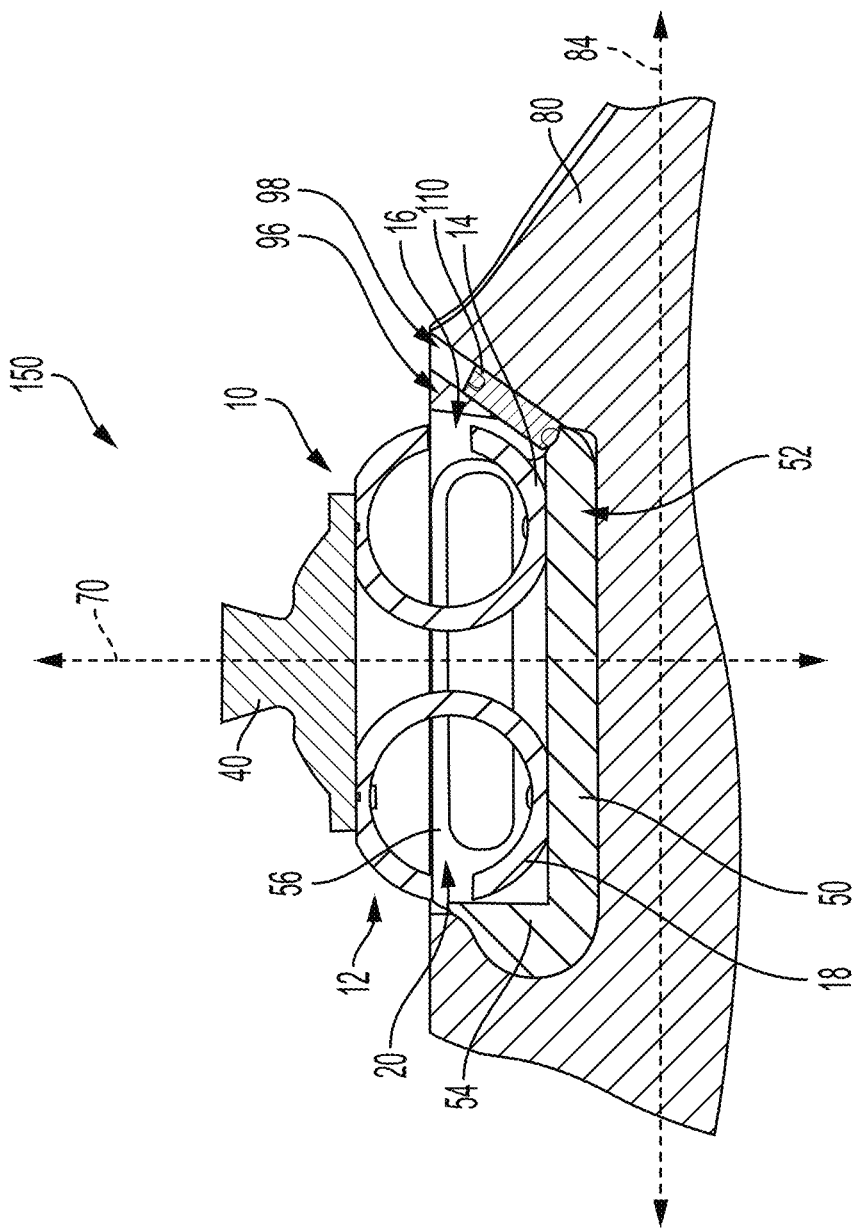

Optionally, in various aspects, and with reference to FIGS. 1A-B, the resilient joint subassembly 12 can have a first spring 14 and a second spring 18. The first spring 14 and the second spring 18 can be spaced apart relative to the longitudinal axis 84 of the prosthetic foot 80. In an exemplary aspect, the first spring 14 and the second spring 18 can be C-springs, although alternative spring types such as, for example, leaf springs, wave springs, and viscoelastic rubber spring elements, are also envisioned. In this aspect, the first spring 14 has an opening 16 and the second spring 18 has an opening 20. The opening 16 of the first spring 14 and the opening 20 of the second spring 18 can permit compression (and then recovery) of the first spring 14 and the second spring 18, respectively, in response to movement of the endoskeletal connector 40 as further disclosed herein. In exemplary aspects, and as shown in FIGS. 1A-1B and 3A-3C, the C-springs can surround respective central axes that are parallel or substantially parallel to each other. In these aspects, it is further contemplated that the central axes of the C-springs can be perpendicular or substantially perpendicular to a plane containing the vertical axis 70 and the longitudinal axis 84 of a prosthetic foot as further disclosed herein.

The first spring 14 and the second spring 18 can differ from one another in at least one of size, stiffness, material, and size of the opening. Thus, in a further aspect, the first spring 14 and the second spring 18 can differ from one another in size. In a still further aspect, the first spring 14 and the second spring 18 can differ from one another in stiffness. For example, the first spring 14 and the second spring 18 can each have a respective rotational stiffness of from about 10 N*m to about 325 N*m, selected according to the body mass of the user. Thus, in various aspects, the first spring 14 (i.e., the spring in the forefoot region) can be stiffer than the second spring 18 (i.e., the spring in the heel region). This can be desirable, for example, to mimic the natural movement of a user. In yet a further aspect, the first spring 14 and the second spring 18 can differ from one another in material. For example, the first spring 14 and the second spring 18 can independently comprise one or more materials selected from steel, stainless steel, titanium, fiber reinforced composites (e.g., glass, aramid, and carbon fibers and various matrix materials), and rubber. In an even further aspect, the first spring 14 and the second spring 18 can differ from one another in the size of the opening, which optionally can be measured as the portion of the circumference of the spring corresponding to the location of the opening (i.e., the circumferential length of the gap between spaced portions of the spring that form the opening). In a still further aspect, the first spring 14 and the second spring 18 can differ from one another in more than one of size, stiffness, material, and size of the opening. In yet a further aspect, the first spring 14 and the second spring 18 can be approximately the same with respect to size, stiffness, material, and size of the opening.

Optionally, in various aspects, and with reference to FIGS. 1A-B, the ankle assembly 10 can have a base 50. The base 50 can be secured to the resilient joint subassembly 12 via, for example and without limitation, at least one fastener (e.g., a screw, a bolt, and the like), welding, and/or an adhesive. Alternatively, the base 50 and the resilient joint subassembly 12 can be a single machined piece or an interlocking structure in which the resilient joint subassembly is geometrically coupled (e.g., connected) to the movements of the endoskeletal connector. In an exemplary aspect, the base 50 can be secured to the first spring 14 and the second spring 18. The first spring 14 and the second spring 18 can be positioned between the base 50 and the endoskeletal connector 40 relative to a vertical axis 70.

Optionally, in additional aspects, the base 50 can be provided as a portion of a carriage 52 that is configured to support the resilient joint subassembly 12. In these aspects, as shown in FIGS. 1A-1B, the carriage 52 can have a rear wall 54 that is shaped to be complementary to a rear surface of the receptacle of a prosthetic foot as further disclosed herein. The carriage 52 can further comprise at least one side wall 56 extending from the rear wall 54 in a forward direction toward the toe portion of the prosthetic foot. Optionally, at least one side wall 56 of the carriage 52 can define an elongate opening 58 to permit gripping of the carriage during insertion and removal of the ankle assembly 10 from the receptacle of the prosthetic foot as further disclosed herein and to reduce the overall weight of the ankle assembly 10.

Figure 2A:
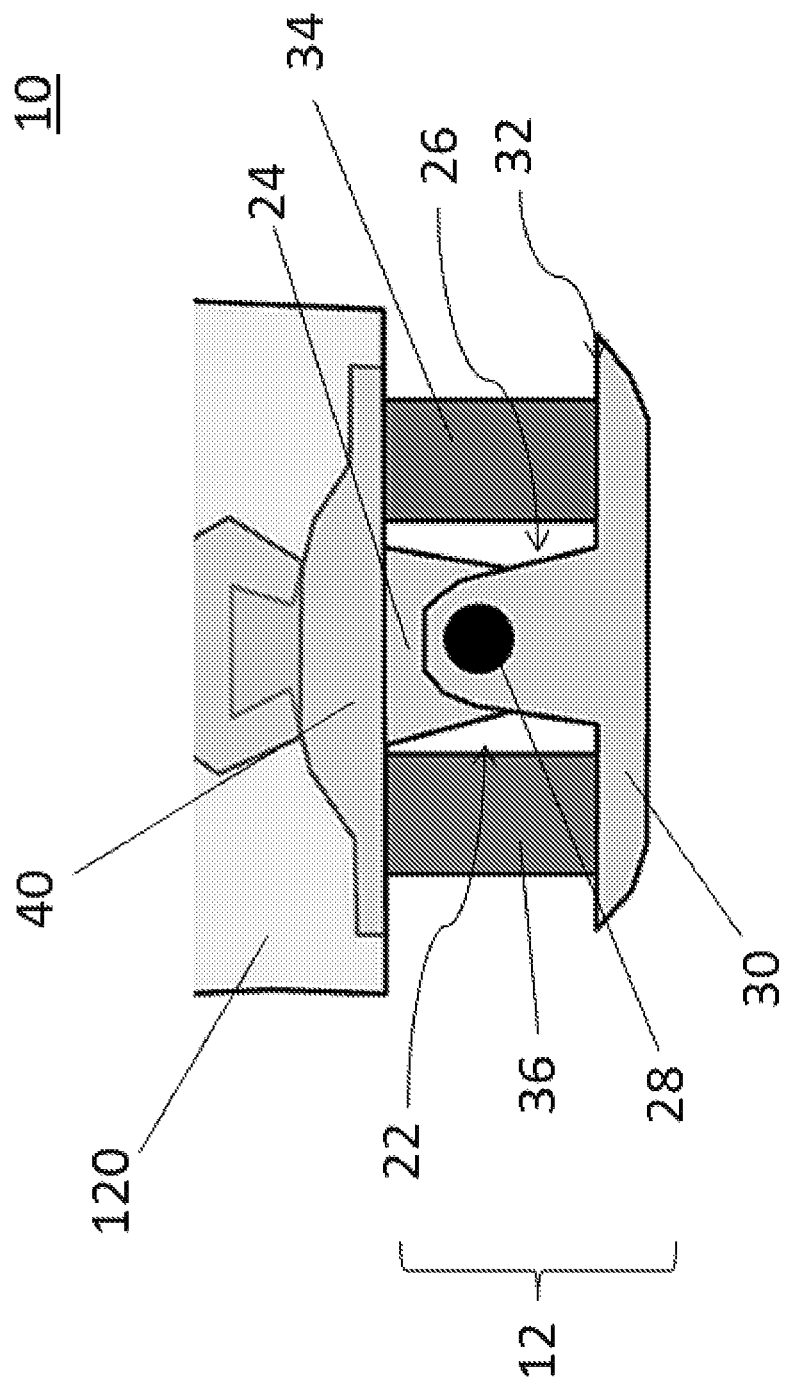
FIG. 2A is partially transparent, side view of an exemplary ankle assembly as disclosed herein, showing connection between the ankle assembly and a prosthetic leg as further described below.
Figure 2B:
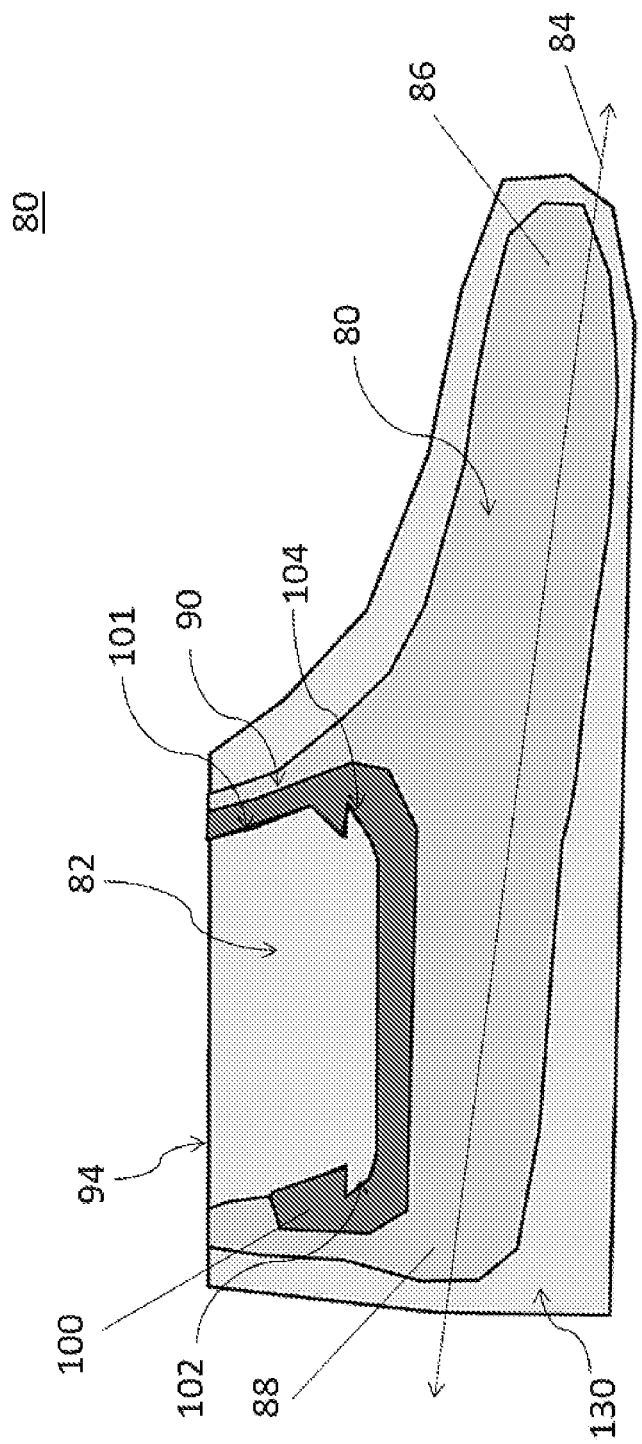
FIG. 2B is a cross-sectional side view of an exemplary prosthetic foot as disclosed herein, with the prosthetic foot defining a receptacle that is configured to receive the ankle assembly of FIG. 2A.
Figure 2C:
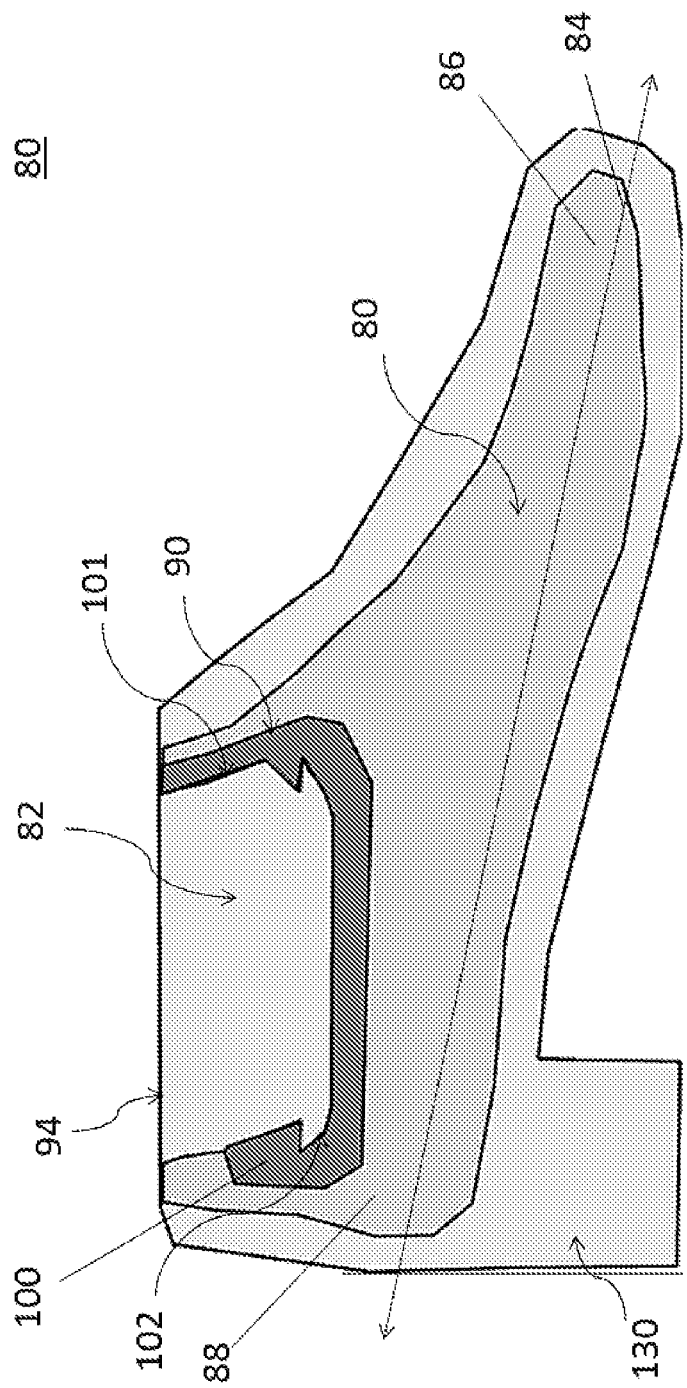
FIG. 2C is a cross-sectional side view of another exemplary prosthetic foot as disclosed herein, with the prosthetic foot defining a receptacle for receiving the ankle assembly of FIG. 2A.

Optionally, in various aspects, and with reference to FIGS. 2A-C and 10A-10B, the resilient joint subassembly 12 can have a mount. As shown in FIGS. 2A-2C, the mount 22 can have a first mount component 24 and a second mount component 26. The first mount component 24 can be secured to the endoskeletal connector via, for example and without limitation, at least one fastener (e.g., a bolt, screw, and the like). The second mount component 26 can be coupled to the first mount component 24 by a pin 28, although alternative pivotal connectors are also envisioned. The pin 28 can be oriented parallel to or in alignment with the transverse pivot axis 60 (see FIGS. 3A-C). In an exemplary aspect, the second mount component 26 has a base portion 30 having a top surface 32. Upon receipt of the resilient joint subassembly 12 within a receptacle 82 of a prosthetic foot 80 (as shown within a shoe 130), the first mount component 24 can be configured for pivotal movement relative to the second mount component 26. More particularly, as further disclosed herein, the base portion 30 of the second mount component 26 can be fixedly engaged by interior surfaces of the receptacle (or an insert) within a prosthetic foot as further disclosed herein, and the first mount component 24, which can be secured in alignment with the connector axis 42 of the endoskeletal connector 40, can pivot relative to the fixedly positioned second mount component.

In exemplary aspects, and as shown in FIG. 2A, the resilient subassembly further comprises a first spring element 34 and a second spring element 36, which are opposed to one another. Optionally, the first spring element 34 and the second spring element 36 can comprise bumpers, which can optionally comprise an elastomer such as, for example, rubber. The first spring element 34 and the second spring element 36 are spaced apart relative to the longitudinal axis 84 of the prosthetic foot 80. Optionally, in various aspects, each of the first spring element 34 and the second spring element 36 are secured to and extend between both the endoskeletal connector 40 and the top surface 32. The first spring element 34 can be positioned between the second spring element 36 and the toe portion 86 and the second spring element 36 can be positioned between the first spring element 34 and the heel portion 88, relative to the longitudinal axis 84, although alternative arrangements are also envisioned. In further optional aspects, the first and second spring elements 34, 36 can be positioned on opposite sides of the pivot pin 28. Optionally, in an exemplary aspect, the first spring element 34 is more rigid than the second spring element 36. For example, the first spring element 34 can be at least 1%, at least 2%, at least 5%, at least 10%, at least 15%, at least 20%, at least 25%, at least 30% or at least 35% more rigid than the second spring element 36. In a further aspect, the first spring element 34 is less rigid than the second spring element 36. For example, the first spring element 34 can be at least 1%, at least 2%, at least 5%, at least 10%, at least 15%, at least 20%, at least 25%, at least 30% or at least 35% less rigid than the second spring element 36. In a still further aspect, the first spring element 34 and the second spring element 36 are equal or substantially equal in rigidity. In an exemplary aspect, the endoskeletal connector 40 is coupled, for example, mechanically coupled, to a prosthetic leg 120 using conventional means that are well-known in the art.

Figure 10A:
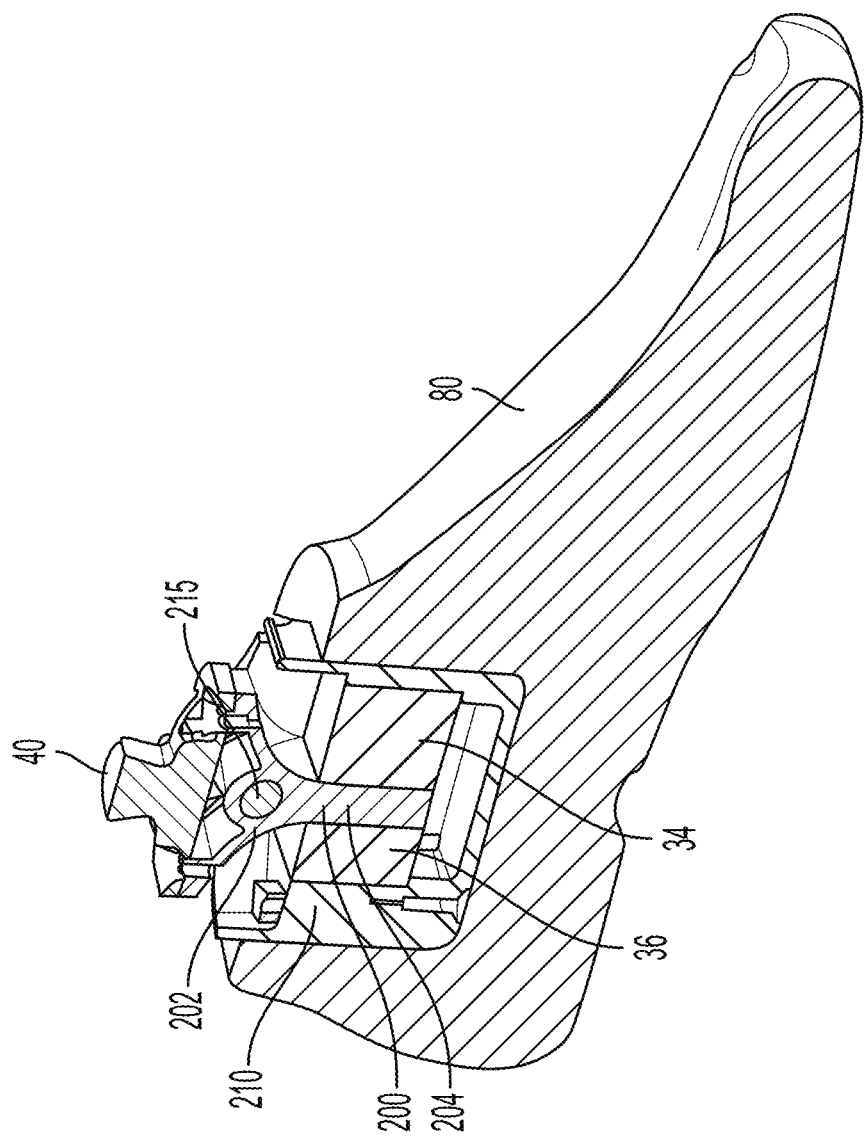
FIG. 10A is a cross-sectional side perspective view of another exemplary foot-ankle system as the ankle assembly is inserted within a receptacle of a prosthetic foot as disclosed herein.
Figure 10B:
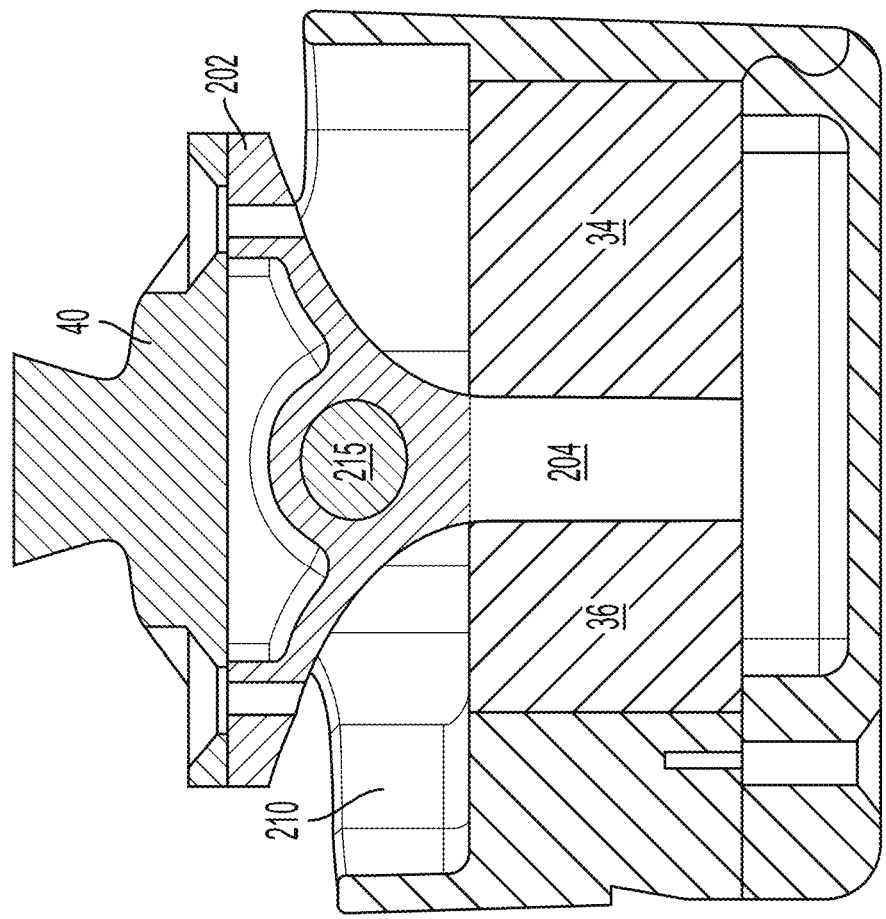
FIG. 10B is a cross-sectional side view of the ankle assembly of the foot-ankle system depicted in FIG. 10A.

Optionally, in various aspects, and with reference to FIGS. 10A-10B, the ankle assembly can further comprise an ankle body 210 having inner surfaces that define a cavity that is configured to receive at least a portion of the resilient joint subassembly 12 and outer surfaces that are configured to engage interior surfaces of a receptacle of the prosthetic foot 80 as further disclosed herein. In these aspects, the mount of the resilient joint subassembly can comprise a mount body 200 (i.e., wiper) comprising resilient material. Optionally, in exemplary aspects, the mount body 200 can comprise one or more metal, alloy, or composite materials, including, for example and without limitation, aluminum alloy, steel, titanium, titanium alloy (e.g., Grade 5 Titanium alloy), magnesium, or carbon fiber-based composite materials. The mount body 200 can have an upper portion 202 secured to the endoskeletal connector 40 and a lower portion 204 extending downwardly from the upper portion. As shown, the upper portion 202 of the mount body 200 can be secured against a lower surface of the endoskeletal connector 40 using one or more fasteners. As further depicted in FIGS. 10A-10B, it is contemplated that the upper portion 202 of the mount body 200 can have a maximum longitudinal dimension (measured relative to the longitudinal axis 84) that is greater than a maximum longitudinal dimension of the lower portion 204. Optionally, it is contemplated that the lower portion 204 can have a generally consistent longitudinal length/thickness (measured relative to longitudinal axis 84), while the upper portion 202 can have a variable length/thickness that increases moving outwardly from the lower portion 204. In further aspects, the ankle assembly can comprise a pin 215 that secures the upper portion 202 of the mount body 200 to the ankle body 210. Optionally, the pin can be rigidly connected to and extend across opposed walls of the mount body 200. In use, it is contemplated that the mount body 200 can be resiliently deformable relative to the pin 215 to provide a range of pivotal motion during forward and backward movement of the joint (i.e., during dorsiflexion and plantar flexion).

As previously discussed, it is contemplated that the resilient joint subassembly can further comprise opposed first and second spring elements 34, 36 that are spaced apart relative to the longitudinal axis 84 of the prosthetic foot 80. As shown in FIGS. 10A-10B, it is contemplated that each of the first and second spring elements 34, 36 can engage one or more inner surfaces of the ankle body 210, and the lower portion 204 of the mount body 200 can be positioned between and in engagement with the first and second spring elements 34, 36. In this configuration, it is contemplated that the first and second spring elements 34, 36 (e.g., bumpers), in combination with the ankle body 210 and the mount body 200, can provide control of dorsi-flexion and plantar-flexion. More particularly, the mechanical properties of the spring elements, the ankle body, and the mount body can determine the range of pivotal motion that is permitted by the ankle assembly. Optionally, in use, it is contemplated that portions (e.g., intermediate portions) of the inner walls of the ankle body 210 can contact the spring elements (e.g., bumpers) 34, 36. It is further contemplated that these portions of the inner walls of the ankle body 210 can be sloped (at a slope angle ranging from about 2 degrees to about 10 degrees) such that the narrowest part of the walls is closest to the pin 215 and the widest part of the walls is farthest from the pin 215. In use, it is contemplated that the slope of these portions of the inner walls of the ankle body 210 can help hold components in place as the mount/body (e.g., wiper) rotates/pivots, deforms relative to the ankle body.

In exemplary aspects, it is contemplated that the ankle body 210 can be configured to conform to the shape of the receptacle in the prosthetic foot to allow for quick attachment of the ankle to the foot. Optionally, in exemplary aspects, it is contemplated that the ankle body 210 can comprise one or more metal, alloy, or composite materials, including, for example and without limitation, aluminum alloy (e.g., ANSI Al-6062-T6 or AL-2024), steel, titanium, titanium alloy (e.g., Grade 5 Titanium alloy), magnesium, or carbon fiber-based composite materials. Optionally, in further aspects, it is contemplated that the endoskeletal connector 40 (and, optionally, a portion of the upper portion 202 of the mount body 200) can extend above the ankle body 210.

In further exemplary aspects, it is contemplated that the size of the receptacle in the prosthetic foot can be slightly larger than the size of the ankle body. For example, following insertion of the ankle body into the prosthetic foot, it is contemplated that the ankle body can have from about 0.002 to about 0.020 inches or about 0.010 inches of clearance on each side of the ankle body. This minimal clearance ensures that there is intimate contact between the bottom surfaces of the ankle body and the receptacle. Optionally, a small fastener (e.g., a screw) can retain the two pieces together in the same manner disclosed in FIG. 1B (see also the landing spot for the screw depicted in FIG. 10B in the lower left portion of the ankle body 210). It is contemplated that because of the geometry between the receptacle and the body, there will be limited load on the fastener (e.g., screw). It is further contemplated that the depth of the pocket and ankle body can be sufficiently large relative to the length such that any mismatch in size does not result in undesired amounts of backlash or lost motion (e.g., slop) during use. In further aspects, it is contemplated that the presence of the slight clearance/tolerance between the ankle body and the receptacle of the prosthetic foot can facilitate a smooth release between the ankle and the prosthetic foot. It is further contemplated that a sloped or tapered inner surface of the receptacle of the prosthetic foot can help guide the ankle body into place.

In various embodiments, the spring elements are described herein as first and second spring elements. However, it should be understood that the present disclosure contemplates the use of a single spring element within the disclosed ankle assemblies. For example, it is contemplated that the spring elements can be provided in the form of a single bumper that extends circumferentially about the lower portion of a mount (or mount body) as disclosed herein.

Figure 3A:
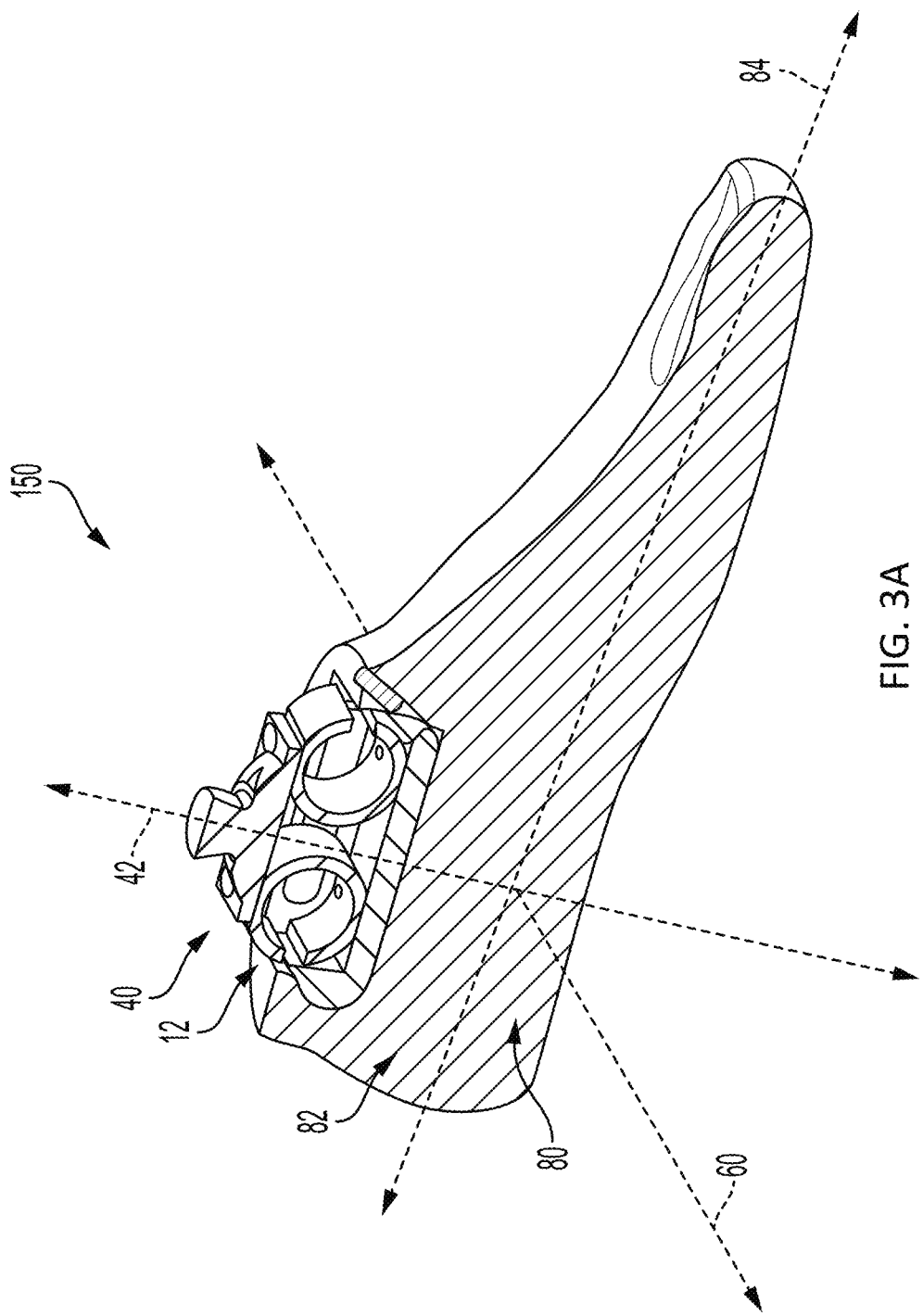
Figure 3B:
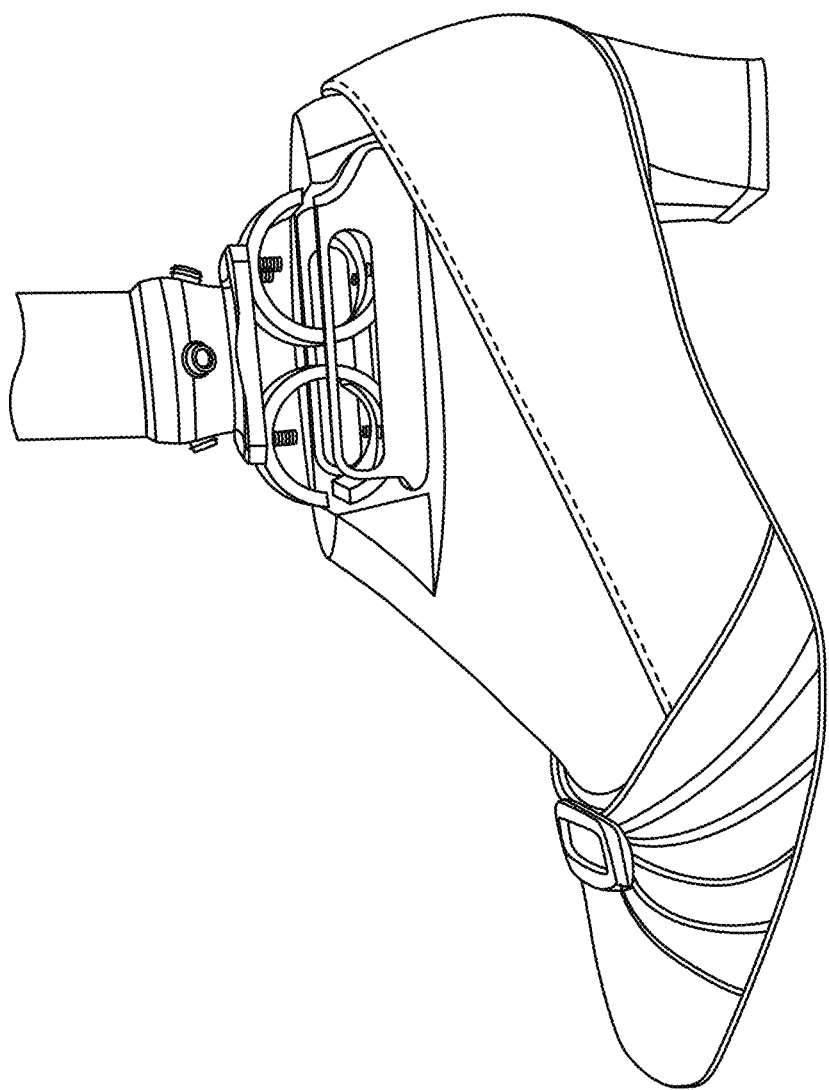
Figure 3C:
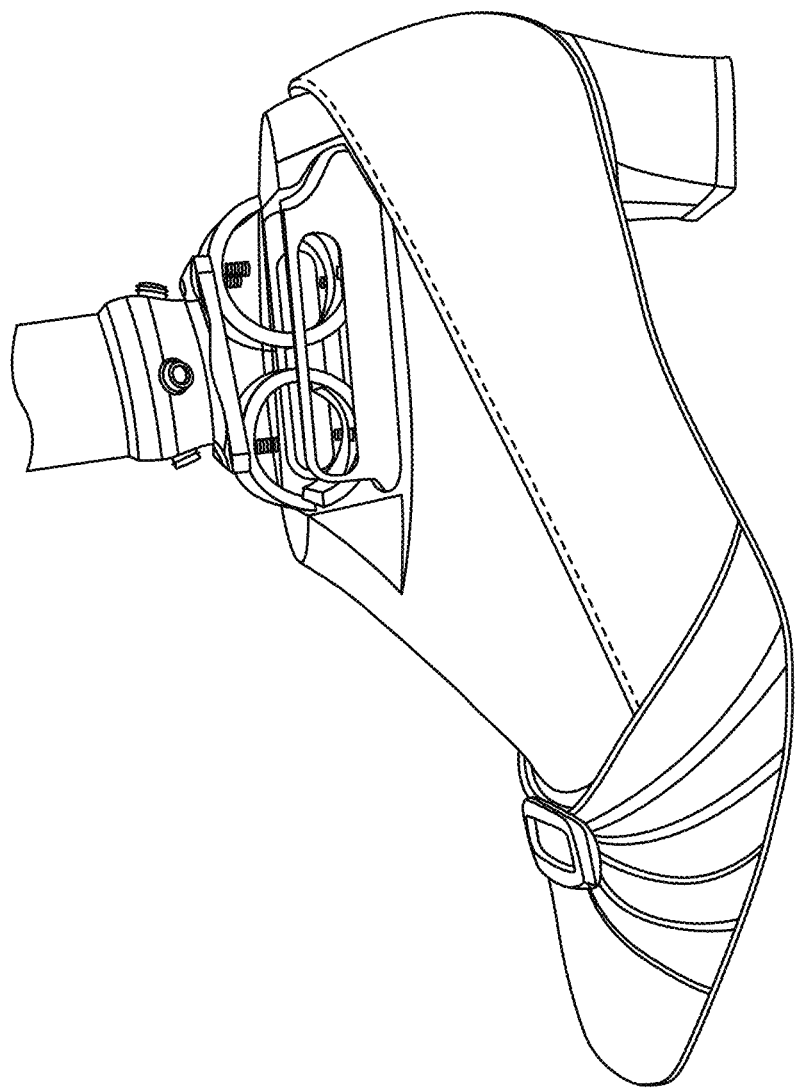
Figure 3D:
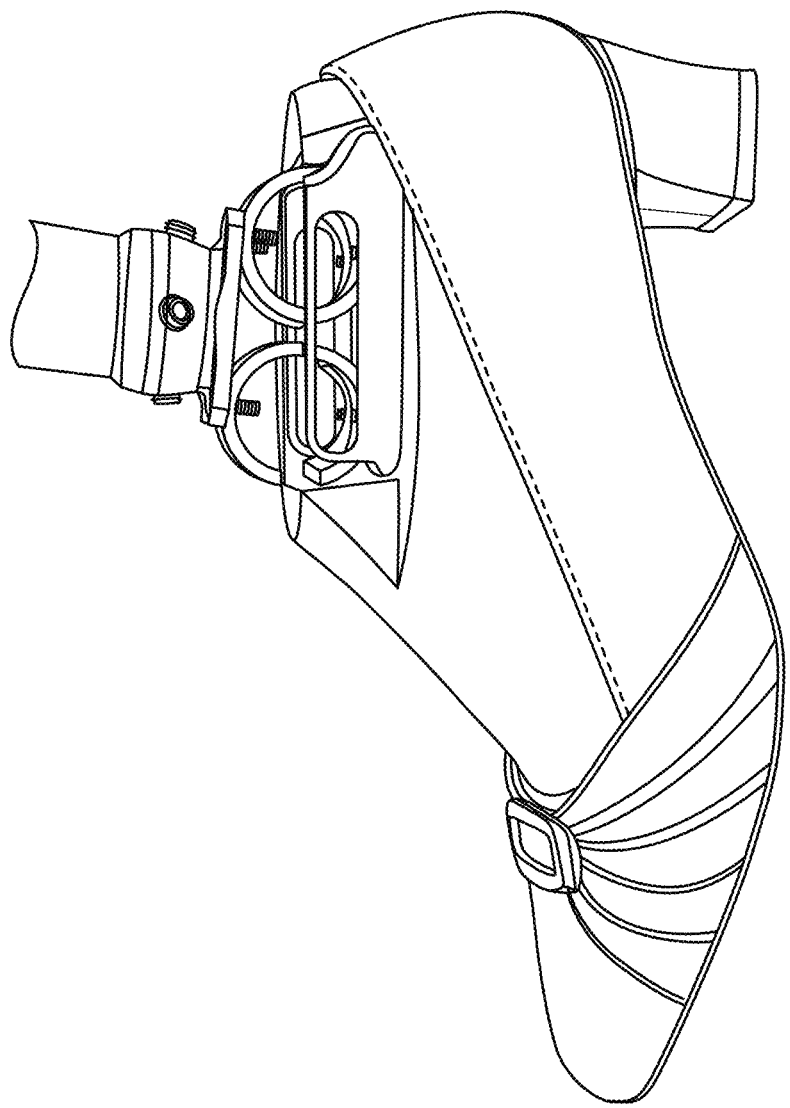
Figure 4A:
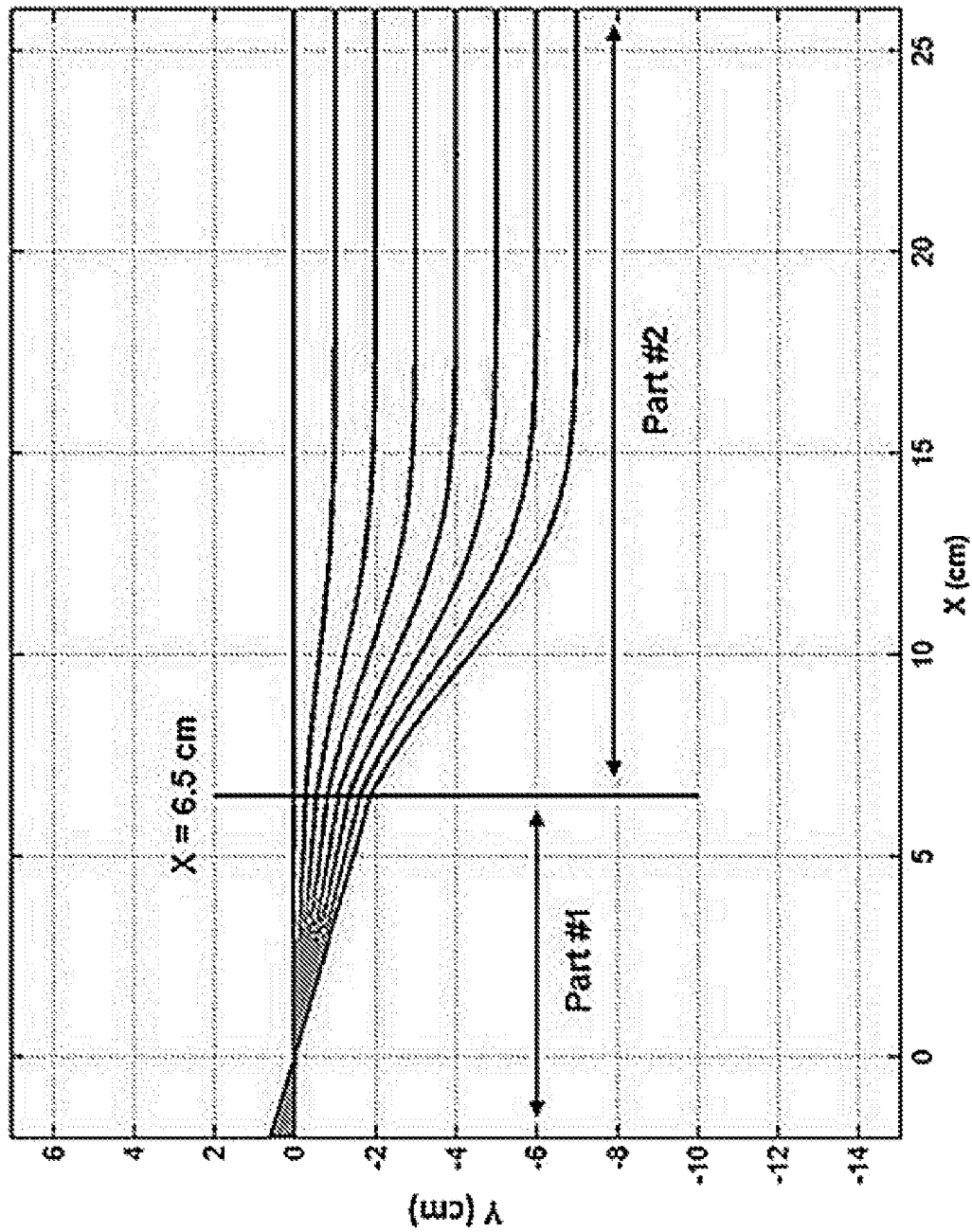
FIGS. 4A-E show representative graphs and images illustrating the plantar insole shapes of shoes as a function of heel height.
Figure 4B:
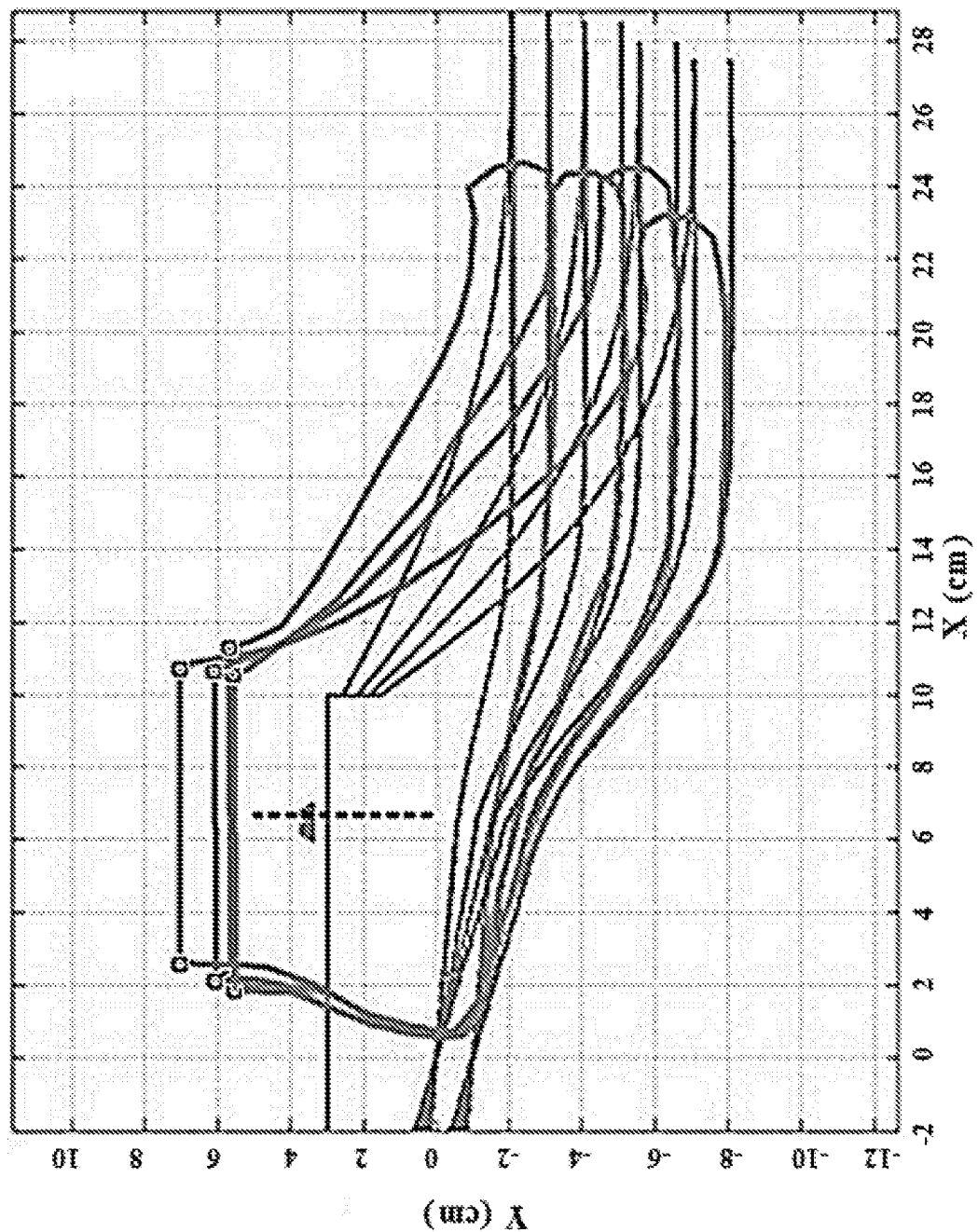
Figure 4C:
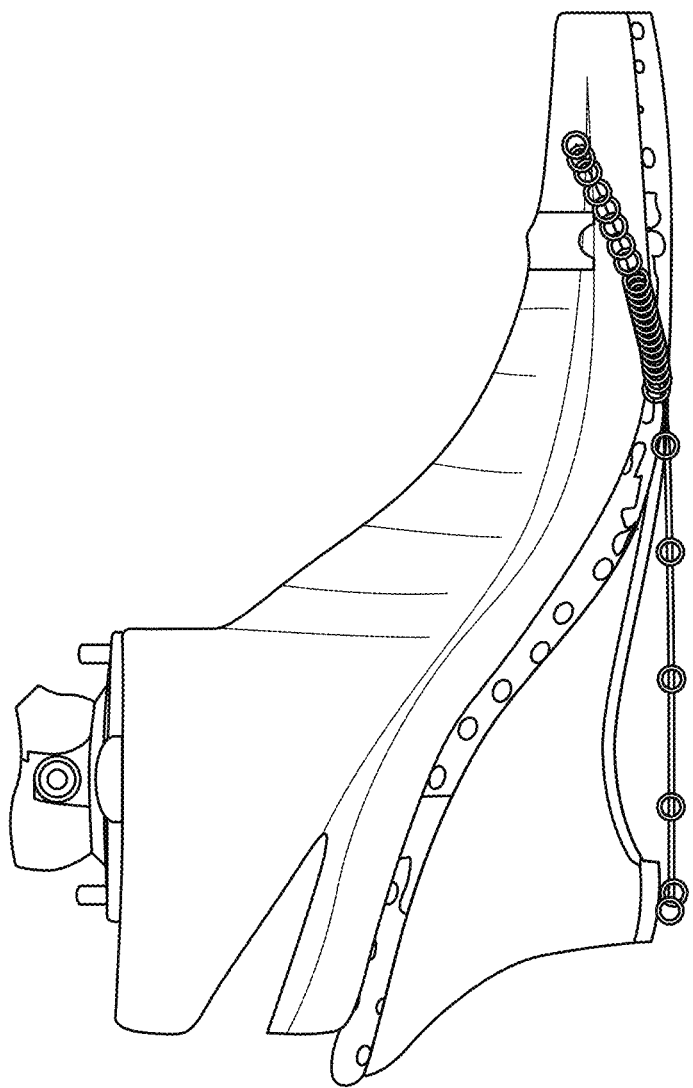
Figure 4D:
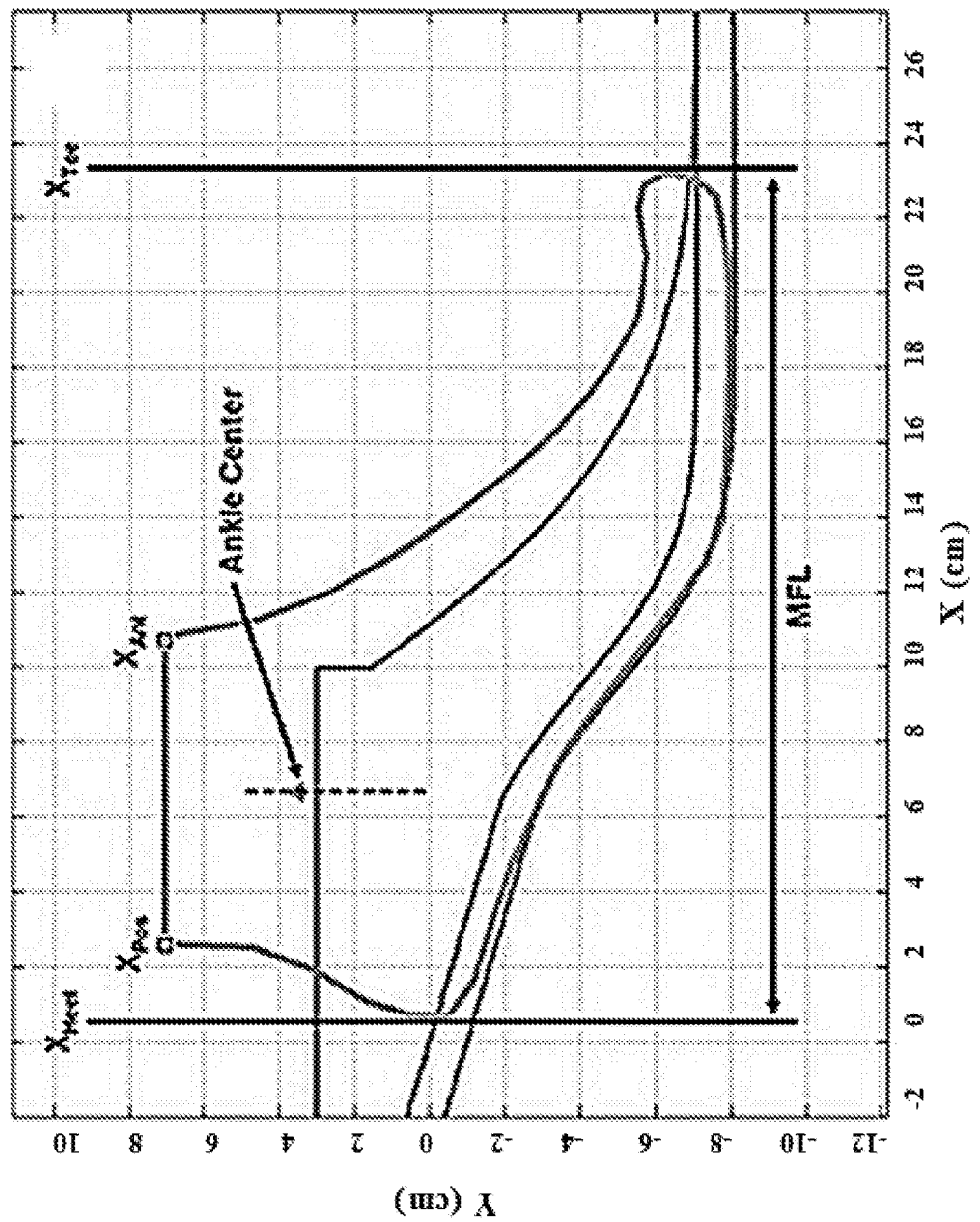
Figure 4E:
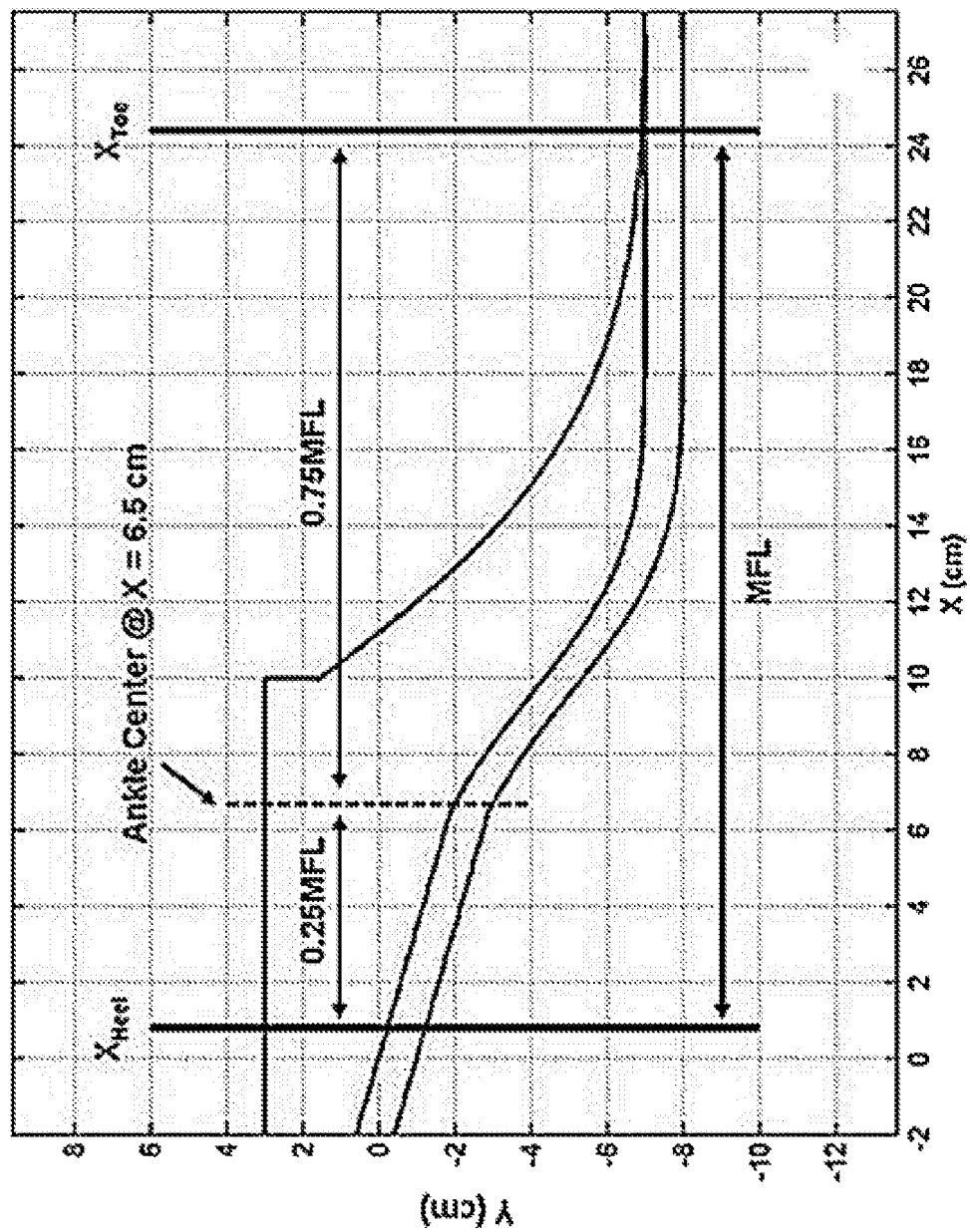

Optionally, in various aspects, and with reference to FIGS. 3A-C, upon receipt of the resilient joint subassembly 12 within the receptacle 82 of the prosthetic foot 80, the resilient joint subassembly 12 is configured to permit pivotal movement of the endoskeletal connector 40 from a start position about a transverse pivot axis 60 that is perpendicular or oblique to the longitudinal axis 84 of the prosthetic foot 80. As used herein, it is understood that the term "pivot axis" refers to a theoretical straight line about which something can pivot. For example, transverse pivot axis 60 refers to a theoretical straight line about which the endoskeletal connector 40 can pivot. Thus, in various aspects, the endoskeletal connector 40 can pivot at least about 10 degrees, at least about 12 degrees, at least about 15 degrees, at least about 17 degrees, at least about 19 degrees, at least about 20 degrees, at least about 22 degrees, at least about 24 degrees, or at least about 25 degrees from a start position about the transverse pivot axis 60. It is contemplated that the amount of pivotal movement relative to the starting or resting position can be represented by an angle θ. Thus, in an exemplary aspect, and with reference to FIGS. 3A and 3E, upon receipt of the resilient joint subassembly 12 within the receptacle 82 of the prosthetic foot 80 (i.e., in a starting or resting position), the endoskeletal connector axis 42 is at an initial angular orientation (i.e., 0=0°). Optionally, at the starting or resting position, the connector axis 42 can be perpendicular or substantially perpendicular to the longitudinal axis 84 of the prosthetic foot. In a further exemplary aspect, and with reference to FIG. 3F, in use, in a forward position (following forward pivotal movement), the endoskeletal connector axis 42' is now located at a first angle 44 relative to the endoskeletal axis 42 in a starting position (i.e., θ>0°), with the first angle 44 ranging from about 5 degrees to about 20 degrees, from about 5 degrees to about 15 degrees, or from about 5 degrees to about 10 degrees, including angles of about 5 degrees, about 6 degrees, about 7 degrees, about 8 degrees, about 9 degrees, about 10 degrees, about 11 degrees, about 12 degrees, about 13 degrees, about 14 degrees, or about 15 degrees. In a still further exemplary aspect, and with reference to FIG. 3G, in use, in a rear position (following rearward pivotal movement), the endoskeletal connector axis 42" is now located at a second angle 46 relative to the endoskeletal axis 42 in a starting position (i.e., θ<0°), with the second angle 46 ranging from about 5 degrees to about 20 degrees, from about 5 degrees to about 15 degrees, or from about 5 degrees to about 10 degrees, including angles of about 5 degrees, about 6 degrees, about 7 degrees, about 8 degrees, about 9 degrees, about 10 degrees, about 11 degrees, about 12 degrees, about 13 degrees, about 14 degrees, or about 15 degrees.

In use, when the patient effects pivotal movement of the endoskeletal connector 40 from the start position to a front position, the first spring (or spring element (e.g., bumper)) can be configured to compress to have a reduced diameter (in response to the force applied, either directly or indirectly, by the endoskeletal connector 40 and/or the mount body). As the patient ceases forward pivotal movement, the energy stored by the first spring (or spring element) can be released to return the first spring to its initial position (and also assist with returning the endoskeletal connector towards the start position). Similarly, when the patient effects pivotal movement of the endoskeletal connector 40 from the start position to a rear position, the second spring (or spring element) can be configured to compress to have a reduced diameter (in response to the force applied, either directly or indirectly, by the endoskeletal connector 40). As the patient ceases rearward pivotal movement, the energy stored by the second spring (or spring element) can be released to return the second spring (or spring element) to its initial position (and also assist with returning the endoskeletal connector towards the start position).

In use, it is contemplated that the first spring element and the second spring element (when provided) can be configured to operate in a similar manner to the first and second springs disclosed herein, with the first spring element storing and releasing energy to assist with returning the endoskeletal connector towards the start position after forward pivotal movement and the second spring element storing and releasing energy to assist with returning the endoskeletal connector towards the start position after rearward pivotal movement.

Thus, in use, during the early stance phase of walking, the ankle assembly rotates backward toward the heel of the prosthetic foot, assisting in shock absorption. As the user moves forward, the energy in the heel of the prosthetic foot is returned to the ankle assembly. The first spring is then compressed as the ankle assembly rotates forward toward the toe of the prosthetic foot. After the opposite foot contacts the ground, the energy in the first spring element or first spring is released back to the user, assisting in the swing phase and/or the forward propulsion of the user.

As further disclosed herein, and with reference to FIGS. 1A-B and 4, it is contemplated that the resilient joint subassembly 12 can be configured for at least partial receipt within a receptacle 82 defined by a prosthetic foot 80 having a longitudinal axis 84. The prosthetic foot 80 can have a toe portion 86 and a heel portion 88 spaced apart relative to the longitudinal axis 84. In an exemplary aspect, when the resilient joint subassembly 12 has a first spring 14 and a second spring 18, the first spring 14 can be positioned between the second spring 18 and the toe portion 86 of the prosthetic foot 80 relative to the longitudinal axis 84. In a further exemplary aspect, when the first spring 14 has an opening 16 and the second spring 18 has an opening 20, the first opening 16 can face the toe portion 86 and the second opening 20 can face the heel portion 88.

Without wishing to be bound by theory, it is contemplated that use of a device for providing biomimetic roll-over shape during walking as disclosed herein can be insensitive to problems encountered by other types of prosthetic systems including, but not limited to a restricted range of motion and user-manipulated alignment.

Foot-Ankle Systems

Also disclosed herein, in various aspects and with reference to FIGS. 1A-3C, is a foot-ankle system configured for use with various shoes having a wide range of different heel heights.

Optionally, in various aspects, and with reference to FIGS. 1A-3C, the foot-ankle system 150 can comprise a prosthetic foot 80 (as shown, within a shoe 130) and an ankle assembly 10 as disclosed herein. As described above, the prosthetic foot 80 can define a receptacle 82 and have a toe portion 86 and a heel portion 88 that are spaced apart relative to a longitudinal axis 84.

Optionally, in various aspects, and with reference to FIGS. 2B-E, the prosthetic foot 80 can have interior surfaces 90 and can further comprise an insert 100 that engages the interior surfaces 90 of the prosthetic foot. Optionally, the insert 100 and the interior surfaces 90 cooperate to define the receptacle 82. Alternatively, the insert 100 can define the entire receptacle 82. The prosthetic foot 80 also defines an opening 94 through which the ankle assembly 10 can be inserted into the receptacle 82. Optionally, in various aspects, the insert 100 has interior surfaces 101. Thus, in an exemplary aspect, at least a portion of the resilient joint subassembly 12 (e.g., the base 50) can be shaped to complementarily engage at least a portion of the interior surfaces 101 of the insert. In various aspects, the interior surfaces 101 of the insert 100 comprise a rear surface 102 that is recessed in a rearward direction (optionally, recessed relative to the opening 94). In still further exemplary aspects, the interior surfaces 101 of the insert 100 can further comprise a front surface 104 that is recessed in a forward direction (optionally, recessed relative to the opening 94). As used herein, the term "recessed" indicates that a surface is inset from surrounding surfaces. Thus, for example, a surface that is recessed relative to an opening cannot be perpendicular to the opening itself (i.e., the surface recedes either rearward or forward relative to the opening).

In use, it is contemplated that the recessed surfaces of the insert 100 can be configured to define respective slots or grooves for receiving a complementary portion of the resilient joint assembly 12 (e.g., end portions of the base 50 or base portion 30 as further disclosed herein) to thereby secure the resilient joint assembly 12 within the receptacle 82.

Optionally, in various aspects, and with reference to FIGS. 1A-B, the prosthetic foot 80 has interior surfaces 90 that define a receptacle 82; that is, the prosthetic foot 80 does not comprise an insert that defines a portion of the receptacle. As described above, the prosthetic foot 80 can define an opening 94 through which the ankle assembly 10 can be inserted into the receptacle 82. Thus, in an exemplary aspect, at least a portion of the resilient joint subassembly 12 (e.g., the base 50 or base portion 30, where provided) can be shaped to complementarily engage at least a portion of the interior surfaces 90. In another exemplary aspect, and with reference to FIGS. 10A-10B, outer surfaces of the ankle body 210 can be shaped to conform to and engage at least a portion of the interior surfaces 90. In various aspects, the interior surfaces 90 can comprise a rear surface 92 that is recessed in a rearward direction (optionally, recessed relative to the opening 94). In still further exemplary aspects, the interior surfaces of the prosthetic foot can further comprise a front surface (not shown) that is recessed in a forward direction (optionally, recessed relative to the opening). In use, it is contemplated that the recessed surface(s) of the interior surfaces of the prosthetic foot can be configured to define respective slots or grooves for receiving a complementary portion of the resilient joint assembly 12 (e.g., end portion(s) of the base 50 or base portion 30 as further disclosed herein) or ankle body 210 (where provided) to thereby secure the resilient joint assembly 12 within the receptacle 82.

Optionally, in various aspects, and with reference to FIGS. 1A-B, the prosthetic foot 80 can define a bore 98 extending between an exterior surface 96 of the prosthetic foot 80 and the receptacle 82. The bore 98, which is accessible from the exterior of the prosthetic foot, can be configured to receive a fastener 110. Examples of fasteners include, but are not limited to, a pin, a screw, a bolt, a cam, and the like. Optionally, in various aspects, the fastener 110 can be provided as a component of the ankle-foot system 150, with the fastener 110 being configured for selective receipt within and selective removal from the bore 98. In use, the fastener 110 selectively engages the base 50 (or other portion of the ankle assembly) within the receptacle 82 of the prosthetic foot 80 to selectively secure the ankle assembly within the receptacle 82 or selectively disengage the ankle assembly to permit removal of the ankle assembly from the receptacle.

Without wishing to be bound by theory, it is contemplated that use of a system for use with different heel heights as disclosed herein can avoid and/or eliminate problems encountered by other types of prosthetic systems including, but not limited to compatibility with a restricted range of heel heights and user-manipulated alignment.

Method of Using the Foot-Ankle System

Further disclosed herein are methods of using the disclosed devices and systems. Thus, in one aspect, disclosed is a method of using a foot-ankle system as disclosed herein and as illustrated in FIGS. 1A-3C.

Optionally, in various aspects, and with reference to FIGS. 1A-3C and 10A-10B, the method comprises using a foot-ankle system 150 as disclosed herein.

Optionally, in various aspects, and with reference to FIGS. 1A-3C, using comprises inserting at least a portion of the resilient joint subassembly 12 of the ankle assembly 10 within the receptacle 82 of the prosthetic foot 80. Optionally, in various further aspects, using further comprises mechanically coupling the ankle assembly 12 to the prosthetic foot 80. As used herein, "mechanically coupling" means indirectly or directly securing or attaching the ankle assembly to the prosthetic foot such that the ankle assembly and prosthetic foot are capable of functioning as a prosthetic foot-ankle joint. Optionally, "mechanically coupling" can include attachment via a fastener, such as, for example and without limitation, a bolt, a pin, a cam, or a screw, or via frictional or other mechanical surface-to-surface engagement. Optionally, in various further aspects, and with reference to FIGS. 2D-E, the endoskeletal connector 40 can be mechanically coupled to a prosthetic leg 120 using conventional mechanisms as are known in the art. Optionally, in various further aspects, the prosthetic foot 80 is positioned within a shoe 130 before the ankle assembly 10 is coupled to the prosthetic foot 80.

Optionally, in various aspects, the method further comprises decoupling the ankle assembly 10 from the prosthetic foot 80 and removing the resilient joint subassembly 12 from the receptacle 82 of the prosthetic foot 80.

Figure 2D:
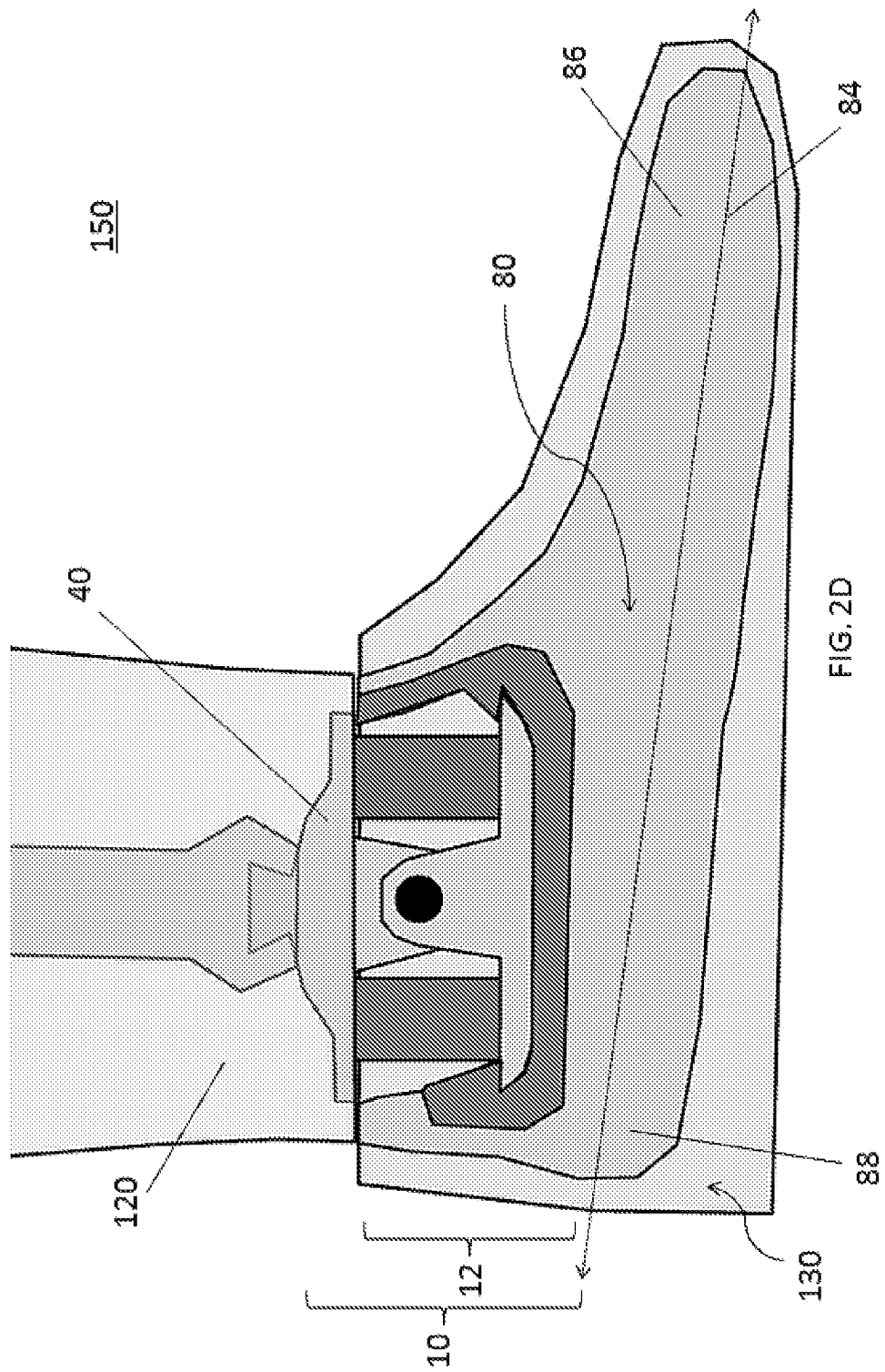
FIG. 2D is a cross-sectional side view of an exemplary foot-ankle system including the ankle assembly of FIG. 2A and the prosthetic foot of FIG. 2B.

Optionally, in various aspects, the prosthetic foot 80 is a first prosthetic foot and the method can further comprise inserting at least a portion of the resilient joint subassembly 12 of the ankle assembly 10 within the receptacle 82 of a second prosthetic foot and mechanically coupling the ankle assembly 10 to the second prosthetic foot. In a further aspect, the second prosthetic foot can have a different shape (e.g., outer profile, height, or angular orientation) than the first prosthetic foot. See, e.g., FIGS. 2D and 2E, showing receipt of the same ankle assembly within two different prosthetic feet, with each prosthetic foot being shaped for complementary receipt within a different shoe. Alternatively, in a still further aspect, the second prosthetic foot has approximately the same shape as the first prosthetic foot. Optionally, in various further aspects, the second prosthetic foot is positioned within a shoe before the ankle assembly 10 is coupled to the second prosthetic foot. See, e.g., FIGS. 2B-2C, showing prosthetic feet received within respective shoes before insertion of the ankle assembly.

Importantly, the devices, systems, and methods disclosed herein can allow for easily changing between shoes of different heel heights without the need for alignment by the user. Additionally, it is contemplated that the disclosed devices, systems, and methods can be effective at closely fitting the plantar shape of a shoe and thus, providing a natural roll-over shape. Further, it is contemplated that the disclosed devices, systems, and methods can be used in a wide range of heel heights while also providing easier fabrication and easier use in comparison with current prosthetic feet.

EXAMPLES

Example 1: Development of a Method for Measuring the Effective Rocker Shapes (Roll-Over Shapes) for Walking A method for measuring the effective rocker shapes of human and prosthetic ankle-foot systems during walking was developed. Briefly, this method involves the transformation of the center of pressure (CoP) of the ground reaction force from a laboratory-based coordinate system to a shank-based coordinate system. In the shank (lower-leg) frame of reference, the CoP draws out the net loading locations on the floor during the stepping cycle (initial contact to opposite initial contact), providing an effective rocker shape that the ankle-foot system conforms to during walking.

Example 2: Ankle-Foot-Shoe Roll-Over Shapes of Able-Bodied Women when Walking with High Heel Shoes Ankle-foot-shoe roll-over shapes of ten able-bodied women, each walking in three different heel height shoes were measured. The ankle-foot-shoe roll-over shapes did not change appreciably in the radius or forward positioning, but primarily shifted downward in the shank-based coordinate systems, reflecting the difference in overall height of the women when walking in the different footwear (Hansen and Childress (2004) *J. Rehabil. Res. Dev.* 41(4): 547-54). It was later discovered that the able-bodied ankle adapts its motion to different shoe rocker radii to maintain similar ankle-foot-shoe roll-over shapes for level walking (Wang and Hansen (2010) *J. Biomech.* 43(12): 2288-93).

Example 3: Alignment of Transtibial Prostheses Based on Roll-Over Shape Principles Seven transtibial prosthesis users, each walking with four different prosthetic feet, were evaluated. The prosthetic feet were intentionally chosen to have a wide variation in roll-over shapes, such that removal of one and replacement with the next (without changes in alignment) would lead to dramatic changes in the roll-over shape in the prosthetic socket frame of reference. After alignment by a highly experienced certified prosthetist, the roll-over shapes of the prosthetic feet were found to nest together toward a theoretical "ideal" roll-over shape for the patient, suggesting the prosthetist is aligning feet toward an "ideal" shape (Hansen et al. (2003) *Prosthet. Ortho. Int.* 27(2): 89-99).

Example 4: Roll-Over Shapes of Prosthetic Feet with Footwear Having Different Heel Heights To determine the effects of different heel height shoes on prosthetic foot roll-over shapes, seven prosthetic feet with a "no heel" shoe (flat sole) and a "low heel" shoe were evaluated. Without alignment adjustments, all of the prosthetic feet had roll-over shapes that were dramatically altered with the different heel height shoes, with rotations of their roll-over shapes in the shank-based reference frame. One of the seven prosthetic feet was a heel height adjustable system named the Total Concept. The Total Concept was tested, first without making adjustments for the alignment, and then again after making alignment adjustments for the low heel shoe. After adjusting the alignment, the roll-over shapes for the two shoes were nearly parallel, mimicking roll-over shapes for able-bodied ankle-foot-shoe systems (Hansen and Childress (2009) *J. of Prosthetics and Orthotics* 21(1): 48-54).

Example 5: Development of Inexpensive Prosthetic Feet (Shape&Roll Talon) for High Heel Shoes Using the knowledge gained from previous studies, low-cost prosthetic feet that were designed to take a biomimetic roll-over shape when used with different footwear and that could be interchanged without a change in alignment were tested. Without wishing to be bound by theory, shoe insole shapes were independent of shoe size and depended only on the heel height of the shoe (i.e., the difference between heel height and forefoot height). A mathematical relationship was developed that closely matched the plantar insole shapes of shoes as a function of the heel height (FIG. 4A-E). This mathematical relationship was used to develop prosthetic foot molds at 1 cm intervals between 0 cm and 7 cm heel height prosthetic feet. Prosthetic feet were then made by compression molding copolymer plastic into foot "dummy" shapes that could be finished into different foot sizes and sides (rights or lefts), following a similar procedure as previously developed for fabrication of the Shape&Roll Prosthetic Foot.

The Shape&Roll Talon feet were tested in three women between the ages of 51 and 65 years. Each woman was asked to bring in one pair of shoes with a flat heel and two high heel shoes, each of their choosing. Talon feet were created for each heel height shoe and the women were instructed on how to interchange the feet. The feet were designed to accommodate the heel height of the shoes such that no alignment changes would be needed when changing from one foot to the next. The women in the study used the feet for five weeks and were encouraged to change feet as many times as they desired. When returning at the end of the five week trial, the women reported changing their feet between once per week to twice a day. The subjects also expressed that they were delighted with the concept and were happy to have had the opportunity to try the prototypes (Meier et al. (2014) *J. Rehabil. Res. Dev.* 51(3): 439-50).

During the study, it was observed that many high heel shoes are extremely stiff between the heel and the forefoot. Although the Shape&Roll Talon was designed to flex along the length of the forefoot (by closing of gaps in the forefoot; see FIG. 4A), it is unlikely that the keels were flexing as designed during walking. This is supported by the flat section of the roll-over shape shown in FIG. 4C. The dots in the roll-over shape show progression of the center of pressure with angular changes of the lower leg (each dot represents one degree of rotation of the lower leg). These dots show a fast forward movement between the heel and forefoot of the foot-shoe system, suggesting a flat effective rocker in this region. Without wishing to be bound by theory, this indicates that the preferred approach to handling high heel shoes is to use stiff feet with flexible ankle joints to allow the necessary flexibility to provide biomimetic function during walking.

Example 6: Modeling to Determine Ankle Stiffness for Rigid Keel Feet

Figure 5A:
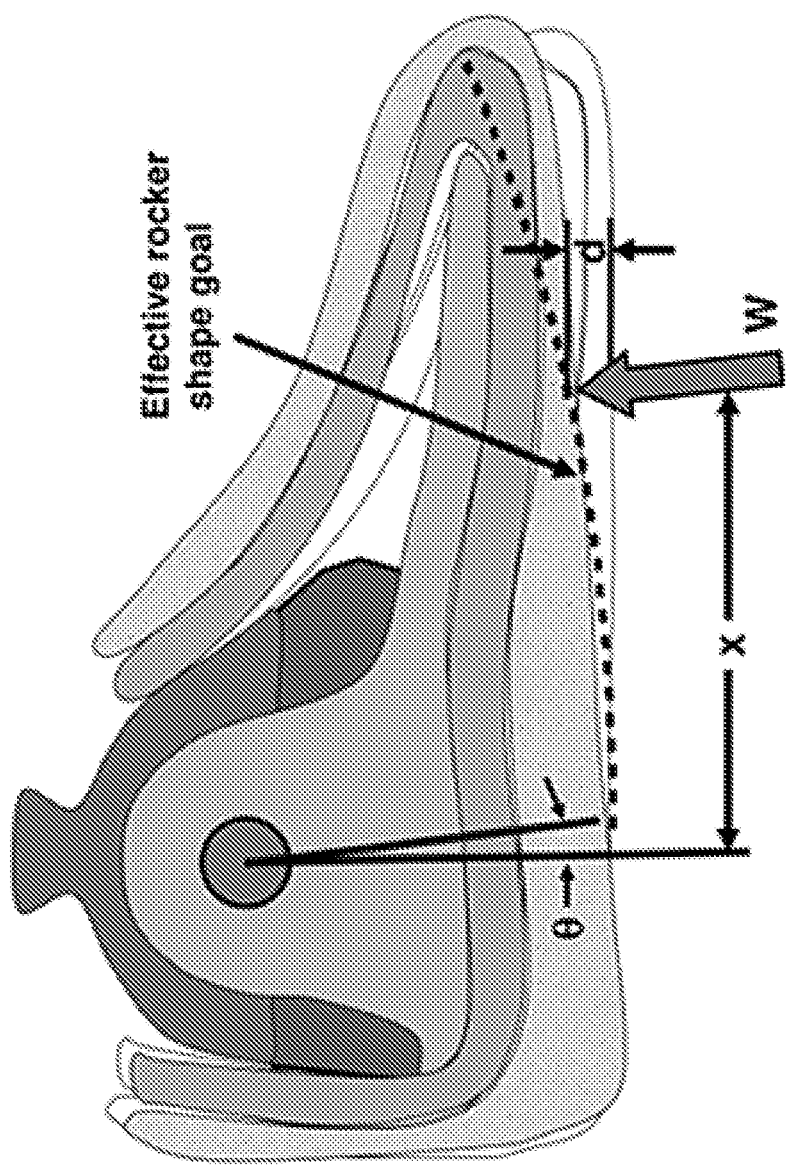
FIGS. 5A-B show representative images and graphs illustrating torsional stiffness for a prosthetic ankle.
Figure 5B:
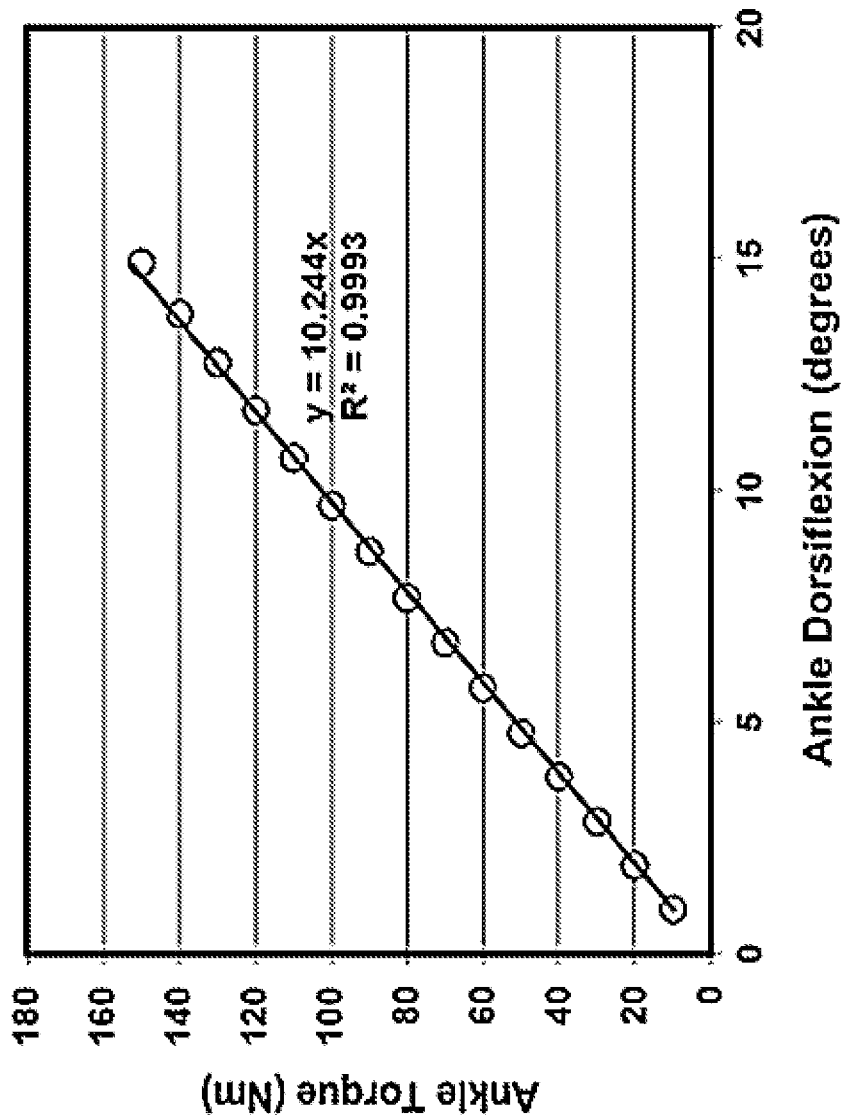
Figure 6A:
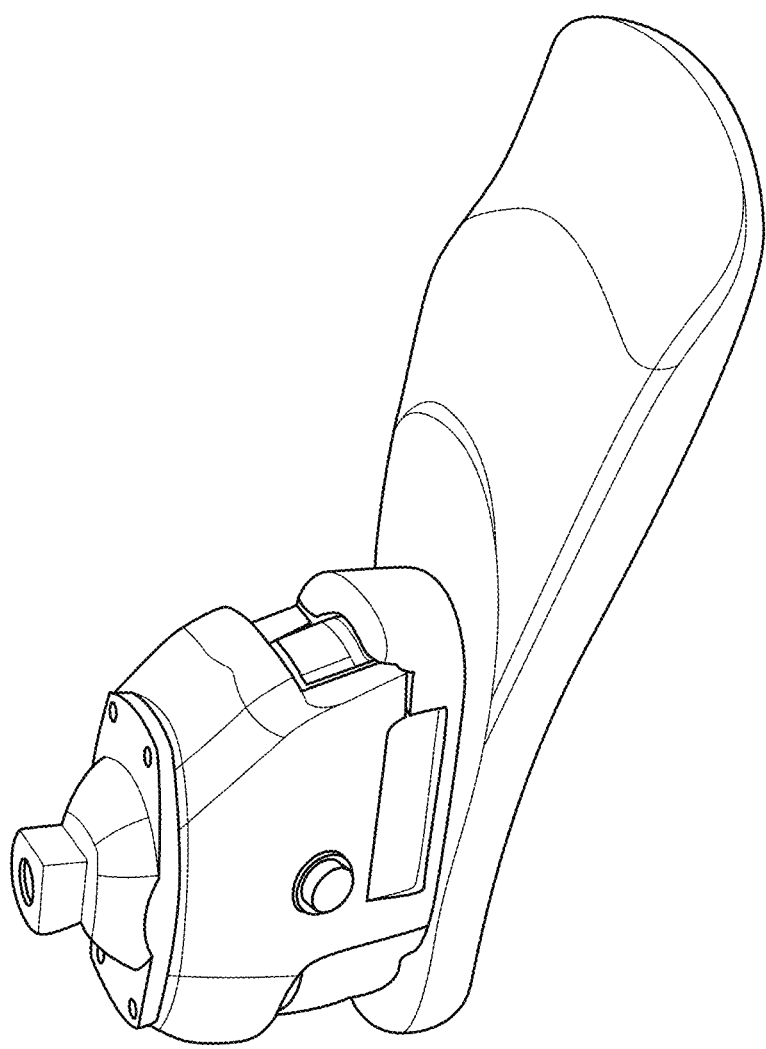
FIGS. 6A-B show representative images of a bimodal ankle-foot system.
Figure 6B:
Figure 7A:
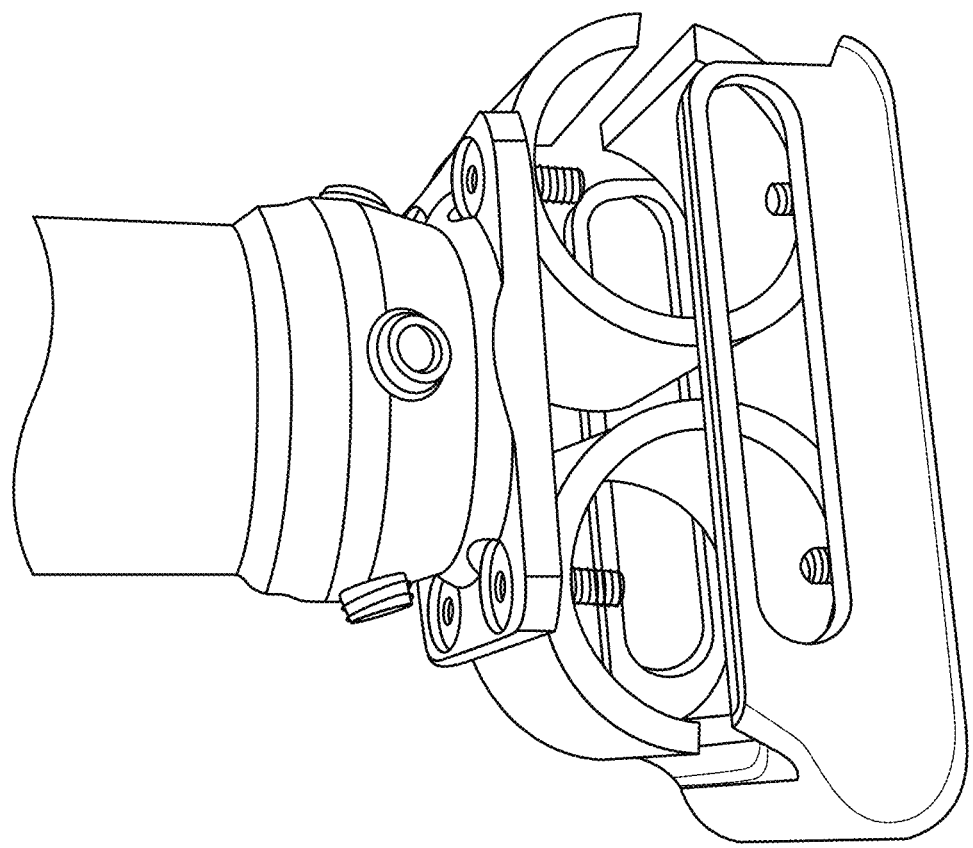
FIGS. 7A-F show representative images of insertion of an exemplary ankle assembly as disclosed herein into the receptacle of a prosthetic foot.
Figure 7B:
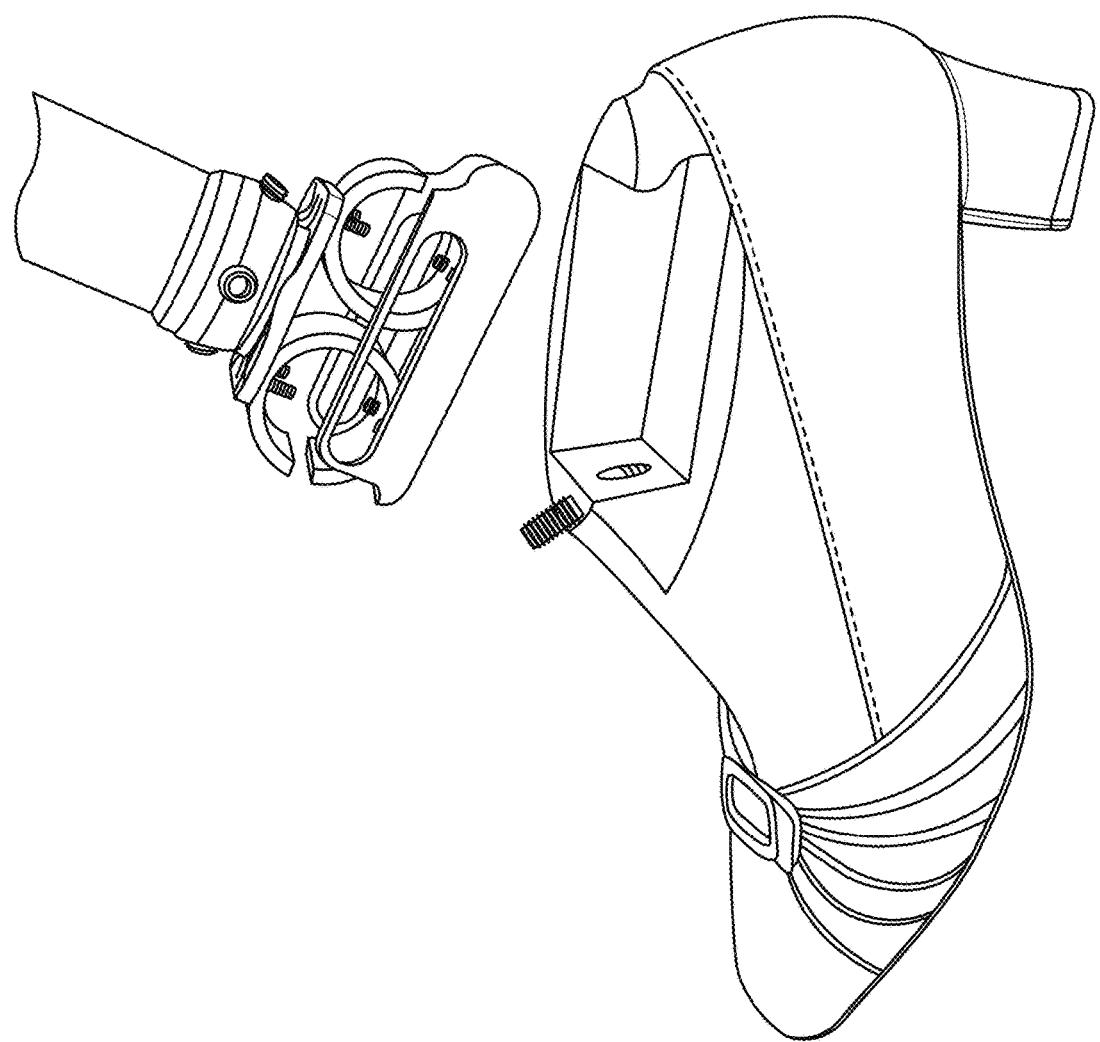
Figure 7C:
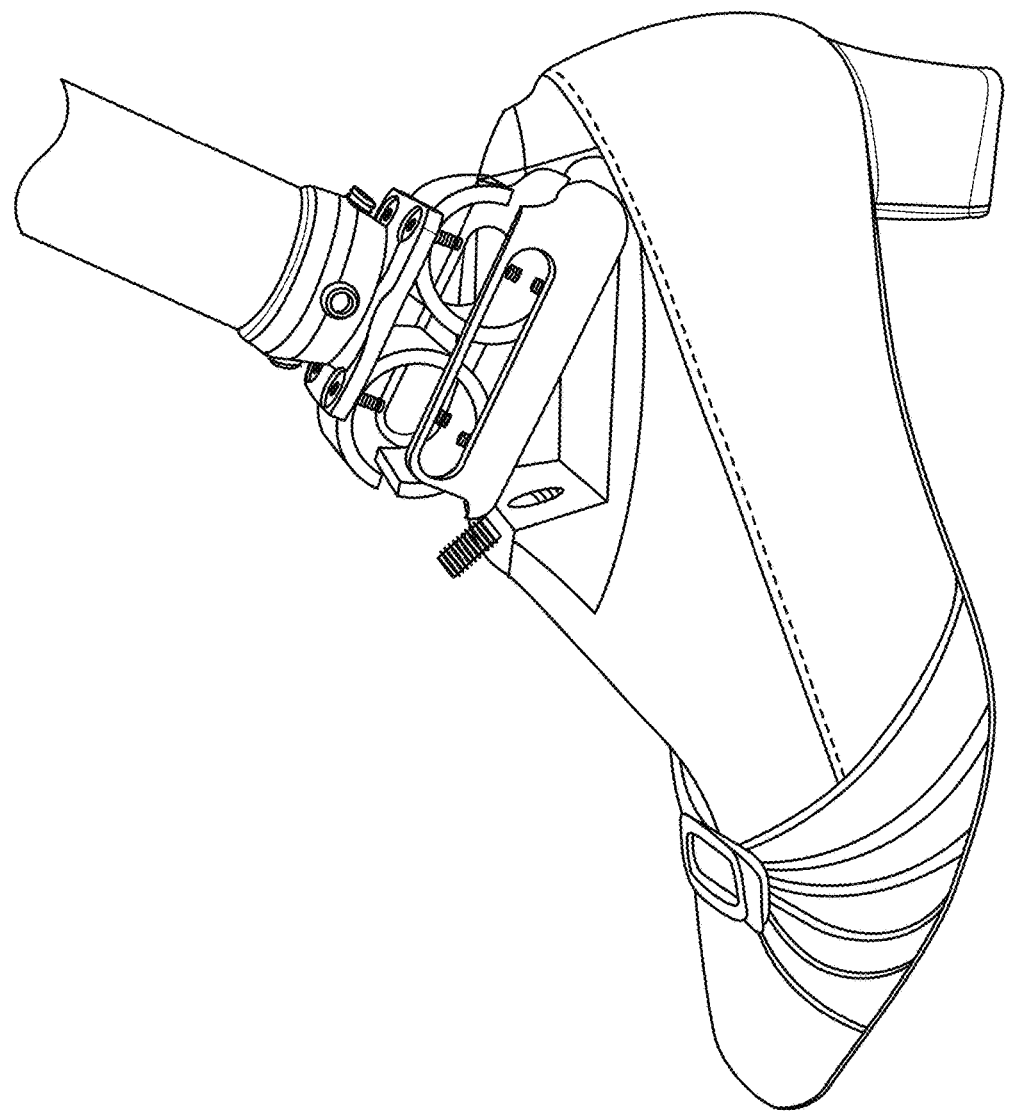
Figure 7D:
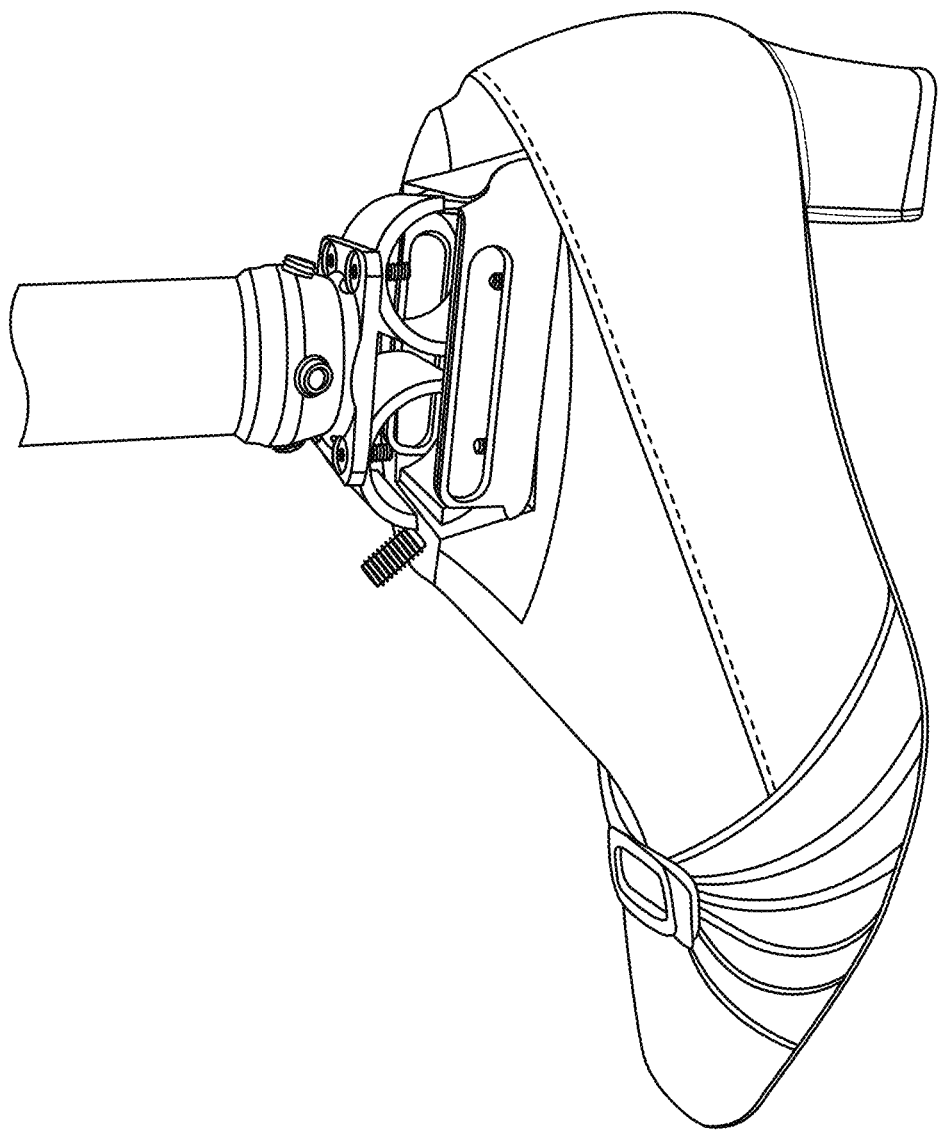
Figure 7E:
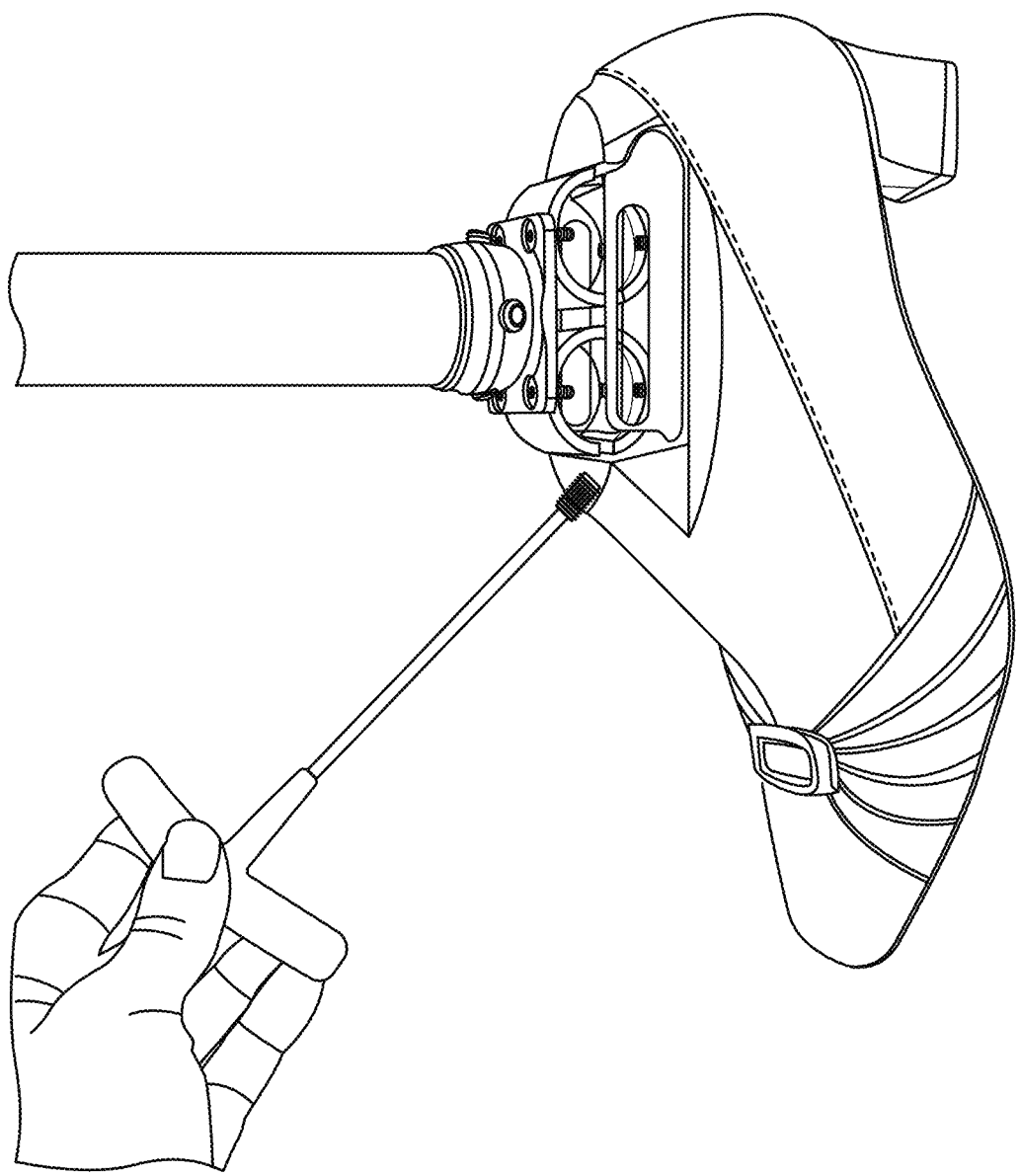
Figure 7F:
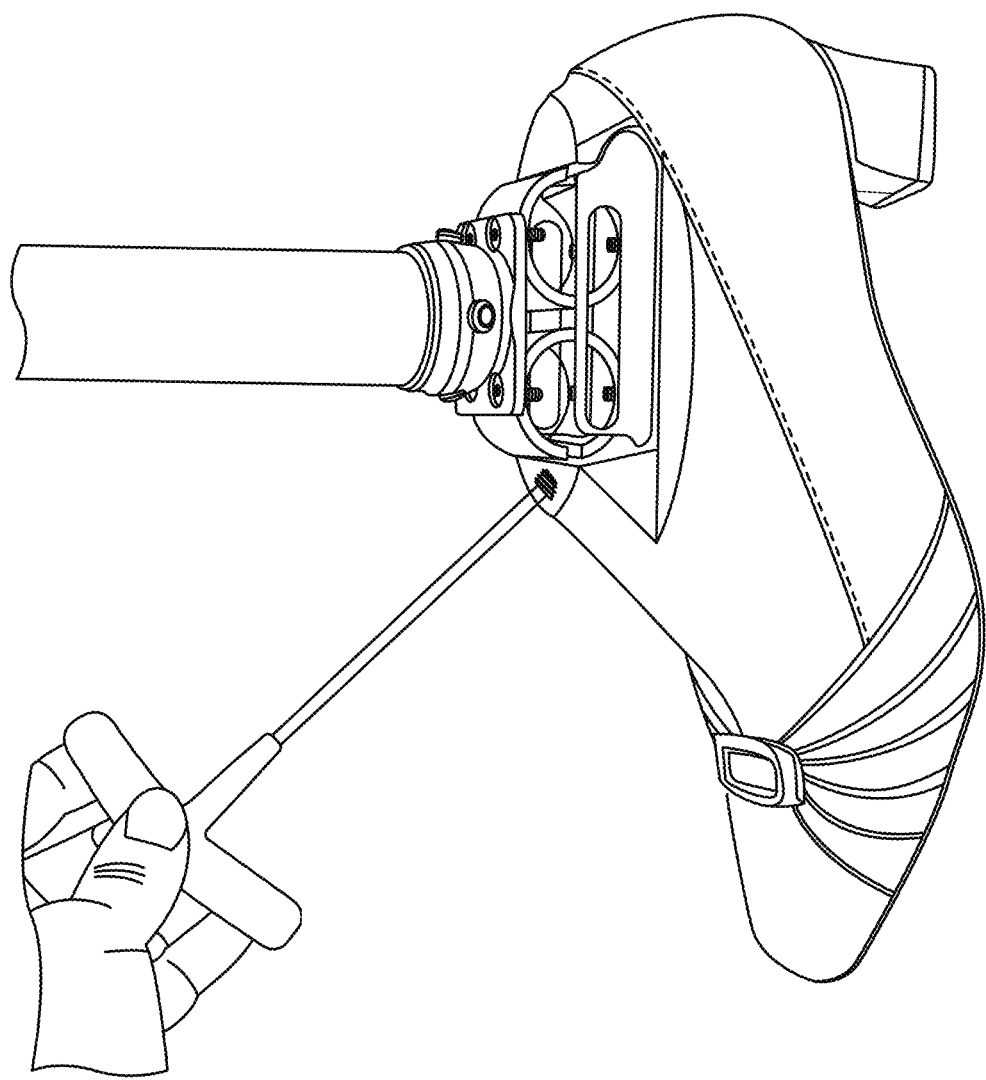
Figure 8A:
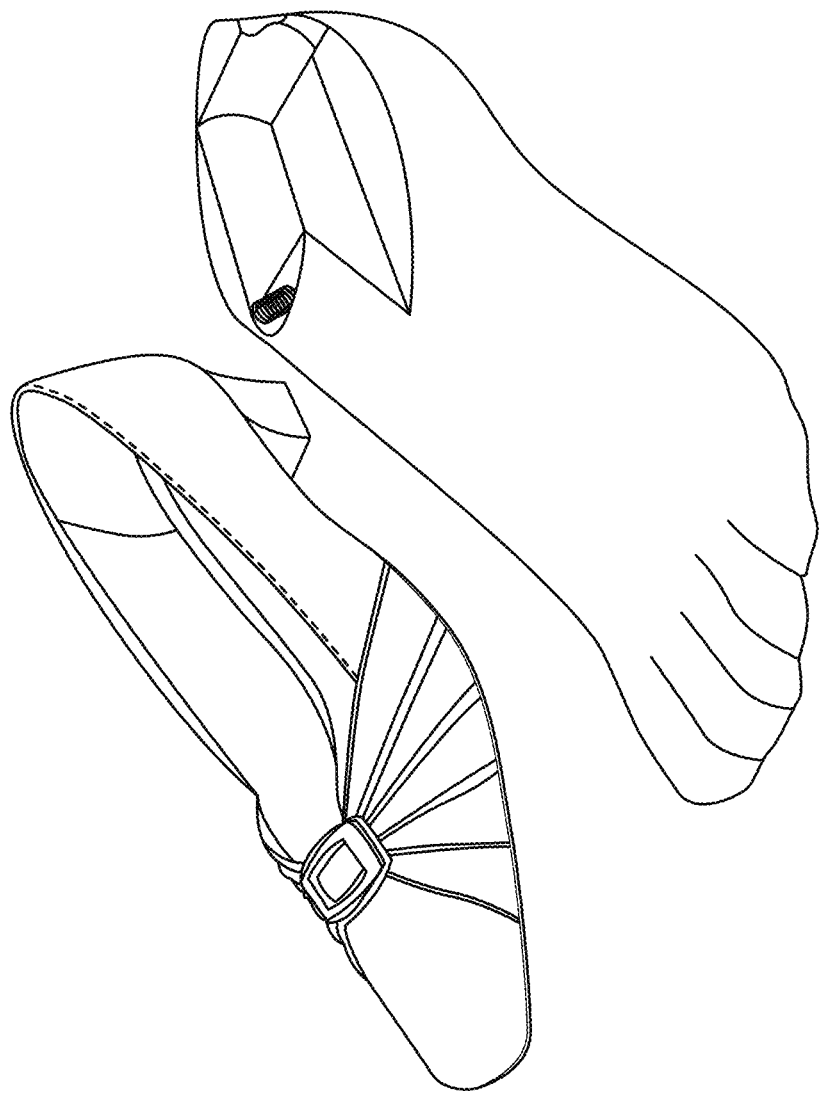
FIGS. 8A-D show representative images of various exemplary prosthetic feet as disclosed herein in shoes of varying heel height. As shown, a side section of the prosthetic feet has been removed to permit viewing of an ankle assembly (not shown) when the ankle assembly is received within the receptacle of the prosthetic foot.
Figure 8B:
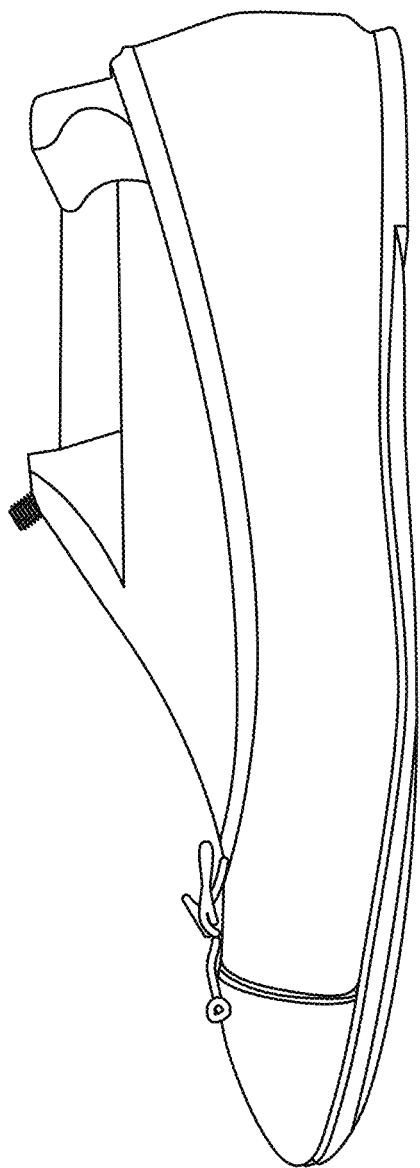
Figure 8C:
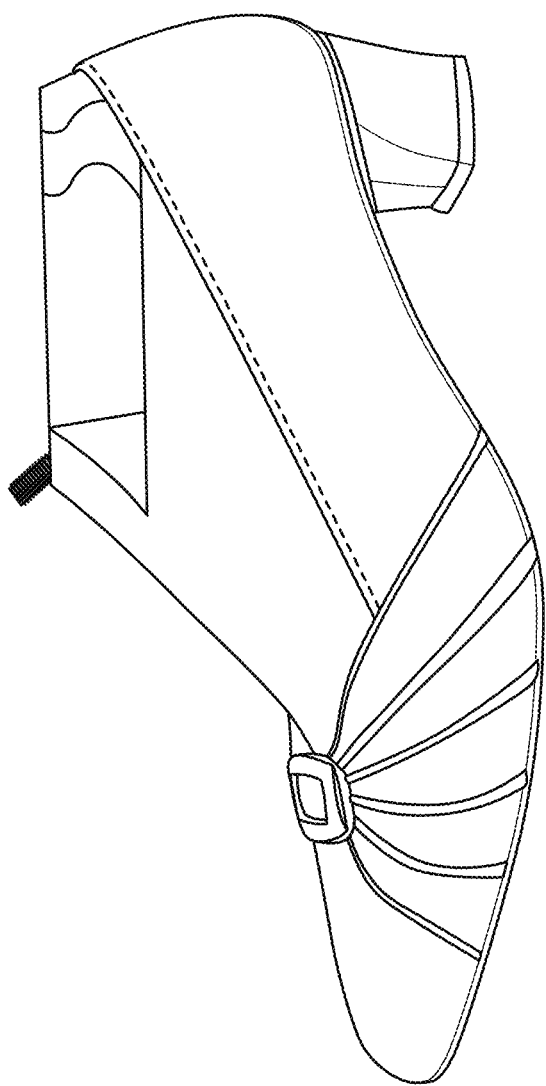
Figure 8D:
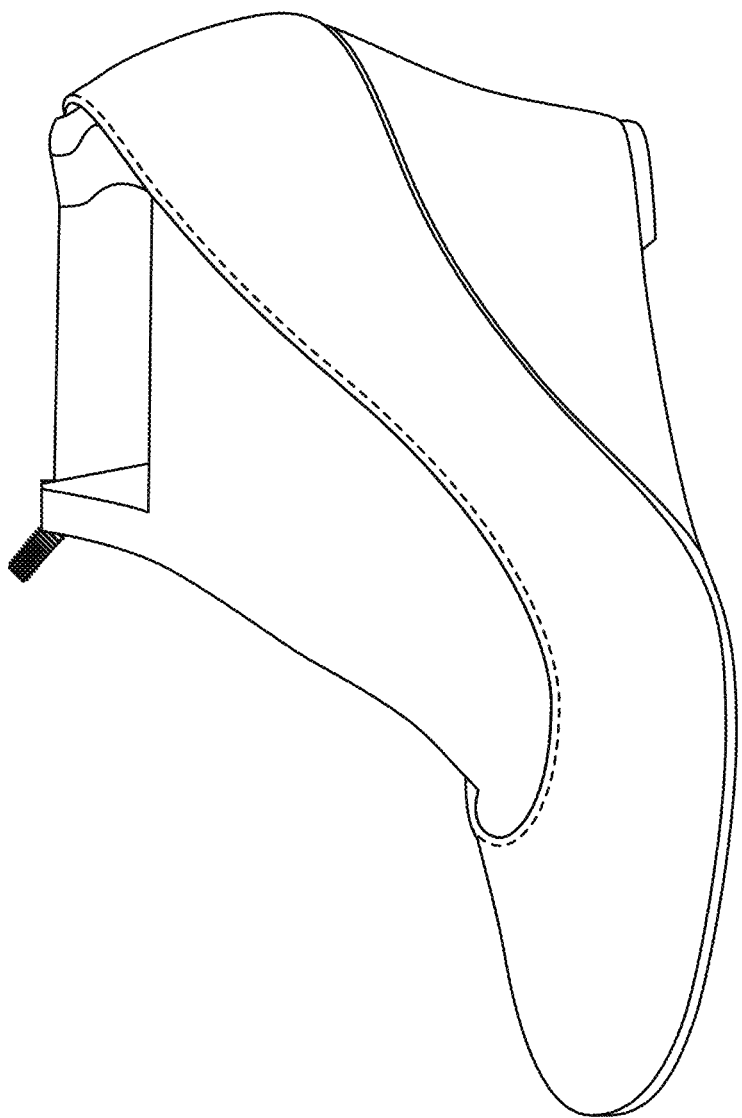
Figure 9A:
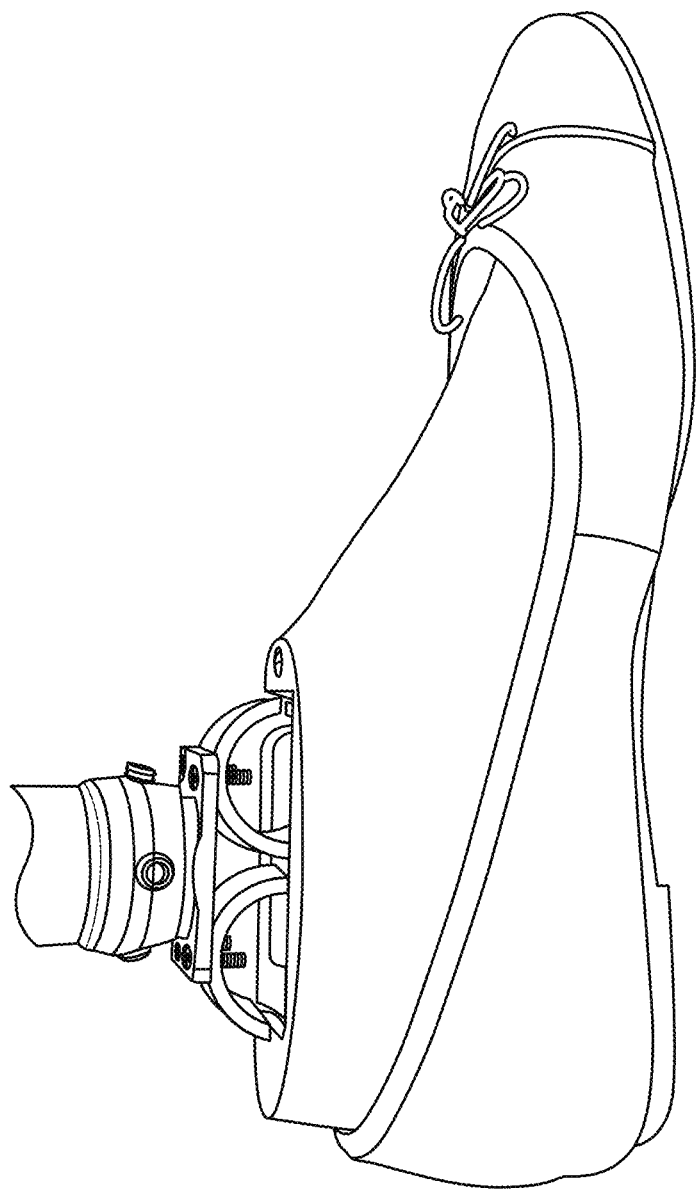
FIGS. 9A-C show representative images of exemplary prosthetic feet and a mechanically coupled ankle assembly as disclosed herein in shoes of varying heel height. The prosthetic feet and the ankle assembly are shown as they would appear during use.
Figure 9B:
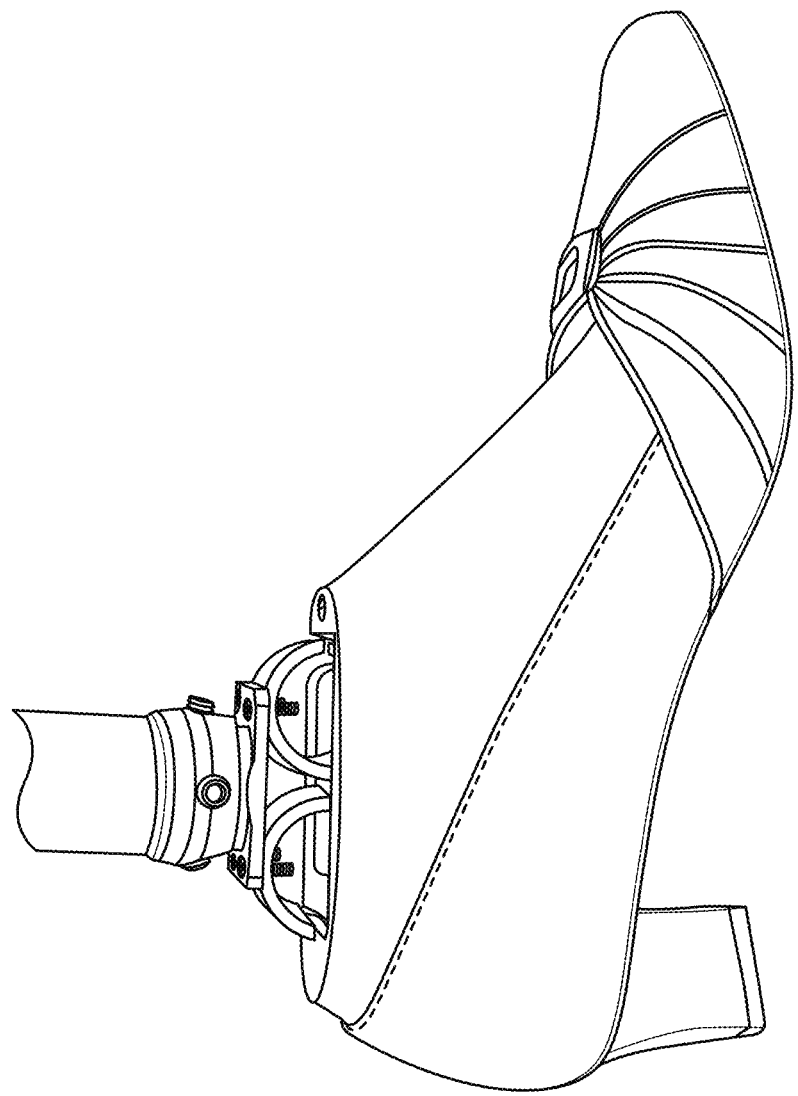
Figure 9C:
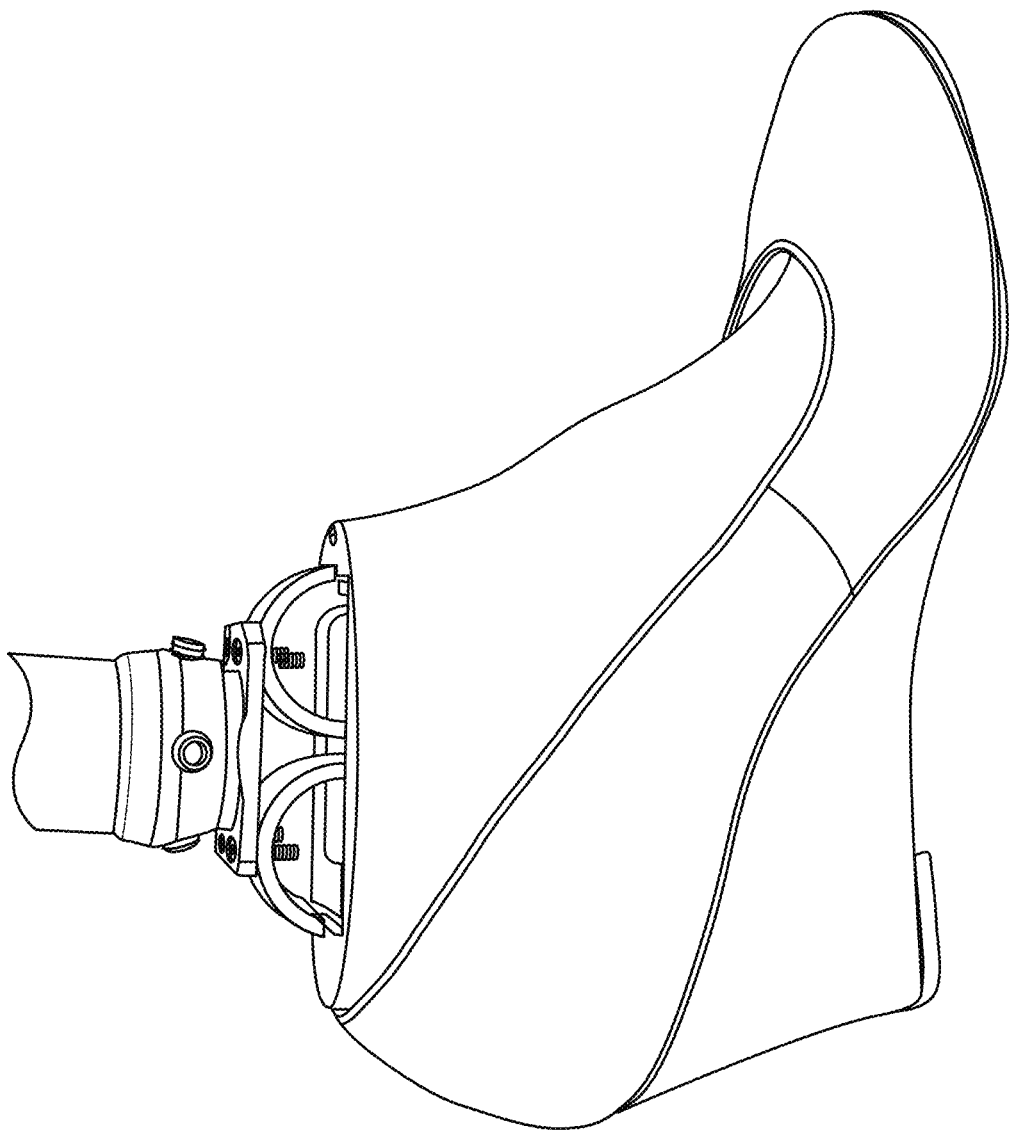

A mathematical model was developed to determine the ankle stiffness levels that could be used with a rigid foot keel to mimic the roll-over shape of able-bodied ankle-foot systems during walking. The model assumes a load (W) applied to the bottom of the foot, which starts anterior to the ankle joint center and progresses toward the toes of the foot (FIG. 5A). At each anterior loading location (x), the ankle must displace an angle (θ) that would yield a vertical displacement (d). The anterior loading location (x) and the vertical displacement (d) are related by the lower arc of a circle ($d = \sqrt{R - R^2 - x^2}$), where R is the best-fit radius of the roll-over shape for walking. For a series of x locations and the effective rocker shape radius (R), the displacement (d) was calculated to match the effective rocker shape goal. At each x location, the angle of rotation of the ankle (θ) was estimated as the arc tangent (d/x) and the torque at the ankle was estimated as the load (W) times the anterior lever arm (x). To determine the stiffness needed in walking, a person with a body weight of 1000 N at anterior locations of 1 cm to 15 cm (in one cm increments) was assumed and the inverse of the curvature for the walking roll-over shape was used as the goal radius for the design. The ankle torque was plotted versus ankle angle and the curve was fit with a line with the intercept set at zero (FIG. 5B). The slope of the line represents the rotational stiffness required to achieve the biomimetic roll-over shape for walking. Without wishing to be bound by theory, this simple analysis can be used to determine the ankle rotational stiffness for a specific patient's body weight and stature (Hansen and Wang (2010) Gait Posture 32(2): 181-4).

Example 7: Rigid Keel Flexible Ankle Designs

Based on the ankle stiffness modeling results described herein above, a biomimetic ankle-foot system with rigid keels and flexible ankles was designed. A 3D-printed keel made of rigid ULTEM™ plastic was connected to a flexible ankle. This ankle-foot system was then tested under walking loads and shown to provide a biomimetic ankle-foot roll-over shape for walking (FIG. 6A-B; Hansen and Nickel (2013) *J. of Medical Devices* 7(3): Article no. 035001).

Data collection of eighteen Veterans with transtibial amputation was conducted. Veterans used the bimodal ankle-foot system for a short time in a laboratory setting. Walking speed and time to complete the L-Test was collected for both their usual prosthetic foot and the bimodal ankle-foot system with ankle unlocked. The flexible ankle rigid keel system did not produce any significant change to mobility of the subjects in terms of walking speed and L-Test times (p>0.05 for both comparisons). Without wishing to be bound by theory, these data suggest the rigid keel flexible ankle approach is functionally viable.

Example 8: Development of a Prosthetic Ankle with a Distal Attachment System for Connection to Custom Prosthetic Feet Small lightweight ankle mechanisms: An ankle with high energy storage and return that will be appropriate for active prosthesis users can be designed. Specifically, an ankle joint that uses two mirrored "C" springs can be developed as shown in FIG. 1A-B. Without wishing to be bound by theory, the initial finite-element modeling suggests that about 15-20 degrees of ankle motion can be achieved with "C" springs made of titanium metals or glass fiber composites, which have favorable Young's modulus vs. strength ratios for this application. Here, titanium "C" springs can be used, although springs made of composite materials such as carbon fiber or glass fiber could also be used for weight reduction, if necessary. This design can allow for a greater stiffness in dorsiflexion than plantarflexion, which is common in prosthetic ankle-foot designs, because early stance plantarflexion will only deform the posterior "C" spring. As the person rolls over onto the forefoot, the anterior "C" spring can contact the upper pyramid connector and be compressed. To accommodate different patient weights and activity levels, different widths and/or thicknesses of "C" springs can be used.

Initial designs of the energy storage and return ankle can be developed in SolidWorks software, with finite element analyses to guide the structural design of the "C" springs. After an initial design is finished, the design can be fabricated and tested in a load frame to determine if the desired rotational stiffness was achieved. Design iterations can continue until the desired ankle stiffness is achieved. ISO 10328 ultimate strength testing can also be done with early designs to find weak points and to refine the design as needed.

In an alternative approach, a single-axis design with rubber spring elements can be used (similar to the design described above for the bimodal ankle project). As detailed above, the current bimodal ankle design was well-liked by the majority of subjects, with 25 some preferring the design to their current energy storage and return prosthetic feet.

The ankle stiffness model shown in FIG. 5A-B can be used to set the rotational stiffness goals for women and men between the 5th and 95th percentile mass and height. Using data for men and women aged 20 years and older and from all racial and ethnic groups, the ankle can be designed for rotational stiffness values for users between 150-190 cm in height and 50-125 kg in mass. The goal roll-over shape radius for the model can be between 16-19% of height for biomimetic walking. Other primary constraints of the ankle are size and mass. The size can be limited to the cosmetic boundary of the lower limb at the ankle and the mass can be constrained to be less than 300 grams. Mass data on 44 commercially available prosthetic ankle-foot systems previously collected ranged from about 450-1200 grams. Also, current Kingsley SACH feet for high heel shoes (size 27 cm) are about 600 grams with the bolt and SACH pyramid adapter. Keeping the ankle to 300 grams or less can allow each foot piece to have a mass of 300 grams or less to match the current mass of the Kinglsey SACH feet.

Other constraints for the ankle can be developed based on tests within the American Orthotics and Prosthetists Association (AOPA) Prosthetic Foot Project (September, 2010), which is incorporated herein by reference in its entirety. This document describes a wide variety of mechanical tests that can be conducted to assist in the recommendation for different L-coding of prosthetic feet.

Lightweight quick-attach mechanisms for exchanging feet: A quick-attach system that allows the user to exchange feet using only a single bolt and without needing to remove the foot from most shoes can be developed. This approach has a tapered rigid receiver in the posterior "heel" region of the foot. This tapered connection can receive the highest tensile stresses on the posterior aspect during the late stance phase of walking. The anterior portion of the foot can have a threaded region with a single bolt (using a threaded insert). The distal end of the ankle can have a taper to fit within the receiver of the foot in the heel region, and can have an angled surface on the anterior end to interface with the single bolt (FIG. 1A-B). The anterior dorsal placement of the single bolt can allow the feet to be easily removed and replaced for lower profile shoes and shoes that have anterior openings. It is noted that this system may still require some footwear to be removed (e.g., tall cowboy boots) prior to disassembly. Alternatively, a system that does not require tools (e.g., using a cam-lock lever similar to those used on bicycle seats) can be used.

Figure 11A:
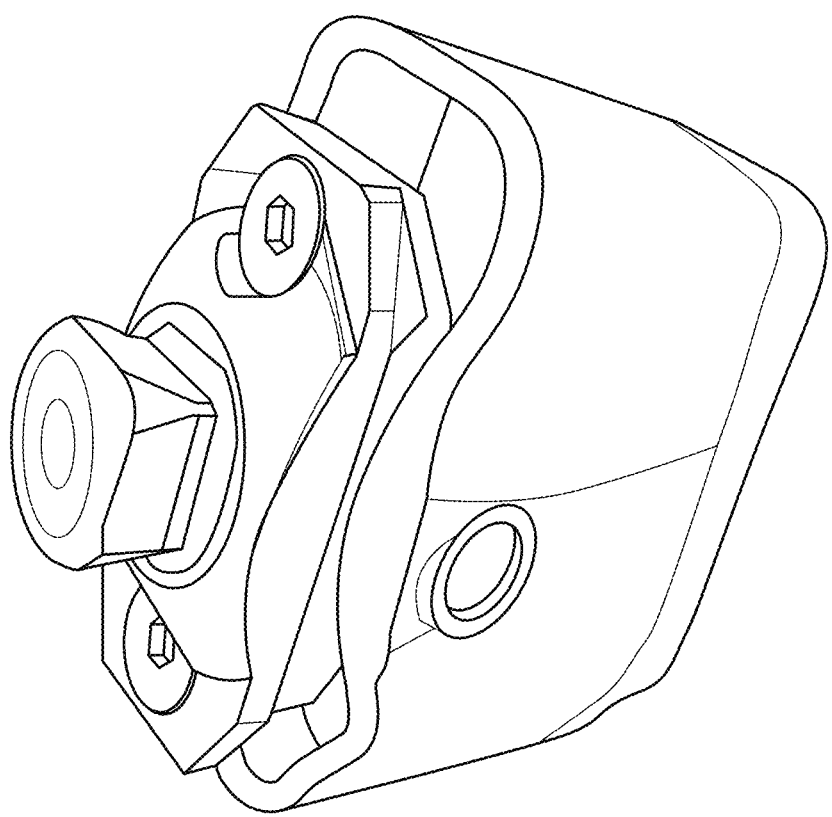
FIG. 11A is an image depicting an experimental ankle unit.
Figure 11B:
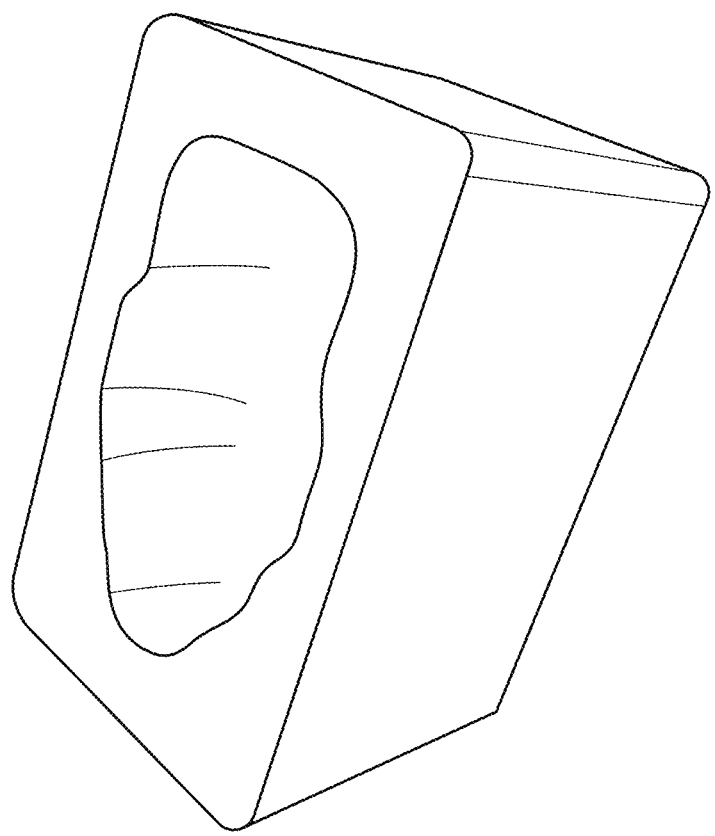
FIG. 11B is an image depicting a pocket receiver for testing of the ankle unit of FIG. 11A.

Example 9: Design of an Articulated Ankle Unit for a Heel-Height Adjustable Prosthesis In another example, with reference to FIGS. 10A-11B, an ankle unit design was created in SOLIDWORKS. Parts were fabricated using CNC milling and machining methods, in accordance with the design (FIG. 11A). The ankle was placed on a rigid mock foot using a pocket receiver (FIG. 11B) to test using a dual-column universal testing machine. Following the guidelines of the American Orthotic and Prosthetic Association ("AOPA's Prosthetic Foot Project," 2010), compressive loads were applied to determine a range of motion (ROM) of the ankle joint. The experimental results showed that the ankle achieved up to 10 degrees ROM in plantarflexion and up to 13 degrees ROM in dorsiflexion. The ROM can be adjusted by modifying or replacing the rubber bumpers within the ankle unit.

EXEMPLARY ASPECTS

In view of the described products, systems, and methods and variations thereof, herein below are described certain more particularly described aspects of the invention. These particularly recited aspects should not, however, be interpreted to have any limiting effect on any different claims containing different or more general teachings described herein, or that the "particular" aspects are somehow limited in some way other than the inherent meanings of the language literally used therein.

Aspect 1: An ankle assembly comprising:
 a resilient joint subassembly configured for at least partial receipt within a receptacle defined by a prosthetic foot having a longitudinal axis and toe and heel portions spaced apart relative to the longitudinal axis; and
 an endoskeletal connector secured to the resilient joint subassembly and configured for mechanical coupling with a prosthetic leg,
 wherein upon receipt of the resilient joint subassembly within the receptacle of the prosthetic foot, the resilient joint subassembly is configured to permit pivotal movement of the endoskeletal connector from a start position relative to a transverse pivot axis that is perpendicular or oblique to the longitudinal axis of the prosthetic foot, wherein upon pivotal movement of the endoskeletal connector in a forward direction toward the toe portion of the prosthetic foot or in a rearward direction toward the heel portion of the prosthetic foot, the resilient joint subassembly is configured to apply a return force to urge the endoskeletal connector toward the start position.

Aspect 2: The ankle assembly of aspect 1, wherein the resilient joint subassembly comprises opposed first and second springs spaced apart relative to the longitudinal axis of the prosthetic foot.

Aspect 3: The ankle assembly of aspect 2, wherein the first and second springs comprise first and second C-springs that define respective openings that permit compression of the first and second C-springs in response to movement of the endoskeletal connector.

Aspect 4: The ankle assembly of aspect 2 or aspect 3, wherein the first and second springs are different in at least one of the following properties: size; stiffness; material; and size of opening.

Aspect 5: The ankle assembly of aspect 3, wherein the first C-spring is positioned between the second C-spring and the toe portion of the prosthetic foot relative to the longitudinal axis of the prosthetic foot, wherein the opening of the first C-spring faces the toe portion of the prosthetic foot, and wherein the opening of the second C-spring faces the heel portion of the prosthetic foot.

Aspect 6: The ankle assembly of any one of aspects 2-5, further comprising a base secured to the first and second springs, wherein the first and second springs are positioned between the base and the endoskeletal connector relative to a vertical axis.

Aspect 7: The ankle assembly of aspect 1, wherein the resilient joint subassembly comprises a mount having:
 a first mount component secured to the endoskeletal connector; and a second mount component coupled to the first mount component by a pin oriented parallel to or in alignment with the transverse pivot axis, wherein the second mount component comprises a base portion having a top surface,
 wherein upon receipt of the resilient joint subassembly within the receptacle of the prosthetic foot, the first mount component is configured for pivotal movement relative to the second mount component.

Aspect 8: The ankle assembly of aspect 7, wherein the resilient joint subassembly further comprises opposed first and second spring elements spaced apart relative to the longitudinal axis of the prosthetic foot, wherein each of the first and second spring elements is secured to and extends between the endoskeletal connector and the top surface of the base portion of the second mount component.

Aspect 9: The ankle assembly of aspect 8, wherein the first spring element is positioned between the second spring element and the toe portion of the prosthetic foot relative to the longitudinal axis of the prosthetic foot, wherein the second spring element is positioned between the first spring element and the heel portion of the prosthetic foot relative to the longitudinal axis of the prosthetic foot, and wherein the second spring element is less rigid than the first spring element.

Aspect 10: The ankle assembly of any one of the preceding aspects, wherein the endoskeletal connector is a pyramid connector.

Aspect 11: A foot-ankle system comprising:
 a prosthetic foot defining a receptacle and having a longitudinal axis and toe and heel portions spaced apart relative to the longitudinal axis; and
 an ankle assembly having:
  a resilient joint subassembly configured for at least partial receipt within the receptacle of the prosthetic foot; and
  an endoskeletal connector secured to the resilient joint subassembly and configured for mechanical coupling with a prosthetic leg,
 wherein upon receipt of the resilient joint subassembly within the receptacle of the prosthetic foot, the resilient joint subassembly is configured to permit pivotal movement of the endoskeletal connector from a start position relative to a transverse pivot axis that is perpendicular or oblique to the longitudinal axis of the prosthetic foot, and wherein upon pivotal movement of the endoskeletal connector in a forward direction toward the toe portion of the prosthetic foot or in a rearward direction toward the heel portion of the prosthetic foot, the resilient joint subassembly is configured to apply a return force to urge the endoskeletal connector toward the start position.

Aspect 12: The foot-ankle system of aspect 11, wherein the resilient joint subassembly comprises opposed first and second springs spaced apart relative to the longitudinal axis of the prosthetic foot.

Aspect 13: The foot-ankle system of aspect 12, wherein the first and second springs comprise first and second C-springs that define respective openings that permit compression of the first and second C-springs in response to movement of the endoskeletal connector.

Aspect 14: The foot-ankle system of aspect 12 or aspect 13, wherein the first and second springs are different in at least one of the following properties: size; stiffness; material; and size of opening.

Aspect 15: The foot-ankle system of aspect 13, wherein the first C-spring is positioned between the second C-spring and the toe portion of the prosthetic foot relative to the longitudinal axis of the prosthetic foot, wherein the opening of the first C-spring faces the toe portion of the prosthetic foot, and wherein the opening of the second C-spring faces the heel portion of the prosthetic foot.

Aspect 16: The foot-ankle system of any one of aspects 12-15, wherein the ankle assembly further comprises a base secured to the first and second springs, wherein the first and second springs are positioned between the base and the endoskeletal connector relative to a vertical axis.

Aspect 17: The foot-ankle system of aspect 11, wherein the resilient joint subassembly of the ankle assembly comprises a mount having:

a first mount component secured to the endoskeletal connector; and a second mount component coupled to the first mount component by a pin oriented parallel to or in alignment with the transverse pivot axis, wherein the second mount component comprises a base portion having a top surface, wherein upon receipt of the resilient joint subassembly within the receptacle of the prosthetic foot, the first mount component is configured for pivotal movement relative to the second mount component.

Aspect 18: The foot-ankle system of aspect 17, wherein the resilient joint subassembly of the ankle assembly further comprises opposed first and second spring elements spaced apart relative to the longitudinal axis of the prosthetic foot, wherein each of the first and second spring elements is secured to and extends between the endoskeletal connector and the top surface of the base portion of the second mount component.

Aspect 19: The foot-ankle system of aspect 18, wherein the first spring element is positioned between the second spring element and the toe portion of the prosthetic foot relative to the longitudinal axis of the prosthetic foot, wherein the second spring element is positioned between the first spring element and the heel portion of the prosthetic foot relative to the longitudinal axis of the prosthetic foot, and wherein the second spring element is less rigid than the first spring element.

Aspect 20: The foot-ankle system of any one of aspects 11-19, wherein the endoskeletal connector is a pyramid connector.

Aspect 21: The foot-ankle system of any one of aspects 11-20, wherein interior surfaces of the prosthetic foot define the receptacle of the prosthetic foot, and wherein the resilient joint subassembly of the ankle assembly is shaped to complementarily engage at least a portion of the interior surfaces of the prosthetic foot.

Aspect 22: The foot-ankle system of aspect 21, wherein the prosthetic foot defines an opening through which the ankle assembly is inserted into the receptacle of the prosthetic foot, and wherein the interior surfaces of the prosthetic foot comprise a rear surface that is recessed in a rearward direction relative to the opening of the prosthetic foot.

Aspect 23: The foot-ankle system of aspect 21 or aspect 22, wherein the ankle assembly comprises a base secured to the first and second springs, wherein the first and second springs are positioned between the base and the endoskeletal connector relative to a vertical axis, and wherein the prosthetic foot defines a bore extending between an exterior surface of the prosthetic foot and the receptacle, wherein the bore is configured to receive a fastener that selectively engages the base within the receptacle of the prosthetic foot.

Aspect 24: The foot-ankle system of aspect 23, further comprising a screw or bolt that is configured for selective receipt within and selective removal from the bore defined by the prosthetic foot.

Aspect 25: The foot-ankle system of any one of aspects 11-20, wherein interior surfaces of the prosthetic foot define the receptacle of the prosthetic foot, wherein the prosthetic foot further comprises an insert that engages the interior surfaces of the receptacle of the prosthetic foot, and wherein the resilient joint subassembly of the ankle assembly is shaped to complementarily engage at least a portion of the insert of the prosthetic foot.

Aspect 26: The foot-ankle system of aspect 25, wherein the prosthetic foot defines an opening through which the ankle assembly is inserted into the receptacle of the prosthetic foot, and wherein the insert of the prosthetic foot comprises a rear surface that is recessed in a rearward direction relative to the opening of the prosthetic foot.

Aspect 27: The foot-ankle system of aspect 25 or aspect 26, wherein the ankle assembly comprises a base secured to the first and second springs, wherein the first and second springs are positioned between the base and the endoskeletal connector relative to a vertical axis, and wherein the prosthetic foot defines a bore extending between an exterior surface of the prosthetic foot and the receptacle, wherein the bore is configured to receive a fastener that selectively engages the base within the receptacle of the prosthetic foot.

Aspect 28: The foot-ankle system of aspect 27, further comprising a screw or bolt that is configured for selective receipt within and selective removal from the bore defined by the prosthetic foot.

Aspect 29: A method comprising:

using a foot-ankle system of any one of aspects 11-28 and 39-40.

Aspect 30: The method of aspect 29, wherein using the foot-ankle system comprises:

inserting at least a portion of the resilient joint subassembly of the ankle assembly within the receptacle of the prosthetic foot; and mechanically coupling the ankle assembly to the prosthetic foot.

Aspect 31: The method of aspect 30, wherein the endoskeletal connector of the ankle assembly is mechanically coupled to a prosthetic leg.

Aspect 32: The method of aspect 30 or aspect 31, wherein the prosthetic foot is positioned within a shoe before the ankle assembly is coupled to the prosthetic foot.

Aspect 33: The method of any one of aspects 30-32, further comprising:
  decoupling the ankle assembly from the first prosthetic foot;
  removing the resilient joint assembly from the receptacle of the prosthetic foot.

Aspect 34: The method of aspect 33, wherein the prosthetic foot is a first prosthetic foot, the method further comprising:
  inserting at least a portion of the resilient joint subassembly of the ankle assembly within the receptacle of a second prosthetic foot; and
  mechanically coupling the ankle assembly to the second prosthetic foot.

Aspect 35: The method of aspect 34, wherein the second prosthetic foot has a different shape than the first prosthetic foot.

Aspect 36: The method of aspect 34 or aspect 35, wherein the second prosthetic foot is positioned within a shoe before the ankle assembly is coupled to the second prosthetic foot.

Aspect 37: The ankle assembly of aspect 1, further comprising an ankle body having inner surfaces that are configured to receive at least a portion of the resilient joint subassembly and outer surfaces that are configured to engage interior surfaces of a receptacle of the prosthetic foot, wherein the resilient joint subassembly comprises a mount having:
  a mount body comprising resilient material and having:
    an upper portion secured to the endoskeletal connector; and
    a lower portion extending downwardly from the upper portion, wherein the upper portion has a maximum longitudinal dimension that is greater than a maximum longitudinal dimension of the lower portion; and
  a pin that secures the upper portion of the mount body to the ankle body, wherein the mount body is resiliently deformable relative to the pin.

Aspect 38: The ankle assembly of aspect 37, wherein the resilient joint subassembly further comprises opposed first and second spring elements spaced apart relative to the longitudinal axis of the prosthetic foot, wherein each of the first and second spring elements engages one or more inner surfaces of the ankle body, and wherein the lower portion of the mount body is positioned between and engagement with the first and second spring elements.

Aspect 39: The foot-ankle system of aspect 11, further comprising an ankle body having inner surfaces that are configured to receive at least a portion of the resilient joint subassembly and outer surfaces that are configured to engage interior surfaces of the receptacle of the prosthetic foot, wherein the resilient joint subassembly comprises a mount having:
  a mount body comprising resilient material and having:
    an upper portion secured to the endoskeletal connector; and
    a lower portion extending downwardly from the upper portion, wherein the upper portion has a maximum longitudinal dimension that is greater than a maximum longitudinal dimension of the lower portion; and
  a pin that secures the upper portion of the mount body to the ankle body, wherein the mount body is resiliently deformable relative to the pin.

Aspect 40: The foot-ankle system of aspect 39, wherein the resilient joint subassembly further comprises opposed first and second spring elements spaced apart relative to the longitudinal axis of the prosthetic foot, wherein each of the first and second spring elements engages one or more inner surfaces of the ankle body, and wherein the lower portion of the mount body is positioned between and engagement with the first and second spring elements.

What is claimed is:

1. An ankle assembly comprising:
  a resilient joint subassembly configured for at least partial receipt within a receptacle defined by a prosthetic foot having a longitudinal axis and toe and heel portions spaced apart relative to the longitudinal axis;
  an endoskeletal connector secured to the resilient joint subassembly and configured for mechanical coupling with a prosthetic leg; and
  an ankle body having inner surfaces that are configured to receive at least a portion of the resilient joint subassembly and outer surfaces that are configured to engage interior surfaces of a receptacle of the prosthetic foot,
  wherein the ankle body has a taper, wherein the taper of the ankle body is configured to engage a sloped or tapered inner surface of the receptacle of the prosthetic foot to cooperate to define a tapered connection having a posterior aspect that is configured to receive a greatest portion of a tensile stress generated during a late stance phase of walking,
  wherein upon receipt of the resilient joint subassembly within the receptacle of the prosthetic foot, the resilient joint subassembly is configured to permit pivotal movement of the endoskeletal connector from a start position relative to a transverse pivot axis that is perpendicular or oblique to the longitudinal axis of the prosthetic foot,
  wherein upon pivotal movement of the endoskeletal connector in a forward direction toward the toe portion of the prosthetic foot or in a rearward direction toward the heel portion of the prosthetic foot, the resilient joint subassembly is configured to apply a return force to urge the endoskeletal connector toward the start position.

2. The ankle assembly of claim 1, wherein the resilient joint subassembly comprises opposed first and second springs spaced apart relative to the longitudinal axis of the prosthetic foot.

3. The ankle assembly of claim 2, wherein the first and second springs are different in at least one of the following properties: size; stiffness; material; and size of opening.

4. The ankle assembly of claim 1, wherein the resilient joint subassembly further comprises opposed first and second spring elements spaced apart relative to the longitudinal axis of the prosthetic foot, wherein the first spring element is configured to bias the endoskeletal connector in a first pivotal direction about the transverse pivot axis, and wherein the second spring element is configured to bias the endoskeletal connector in a second pivotal direction about the transverse pivot axis that is opposite the first pivotal direction.

5. The ankle assembly of claim 4, wherein the first spring element is positioned between the second spring element and the toe portion of the prosthetic foot relative to the longitudinal axis of the prosthetic foot, wherein the second spring element is positioned between the first spring element and the heel portion of the prosthetic foot relative to the longitudinal axis of the prosthetic foot, and wherein the second spring element is less rigid than the first spring element.

6. The ankle assembly of claim 1, wherein the resilient joint subassembly comprises a mount having:
   a mount body having:
      an upper portion secured to the endoskeletal connector; and
      a lower portion extending downwardly from the upper portion; and
   a pin that secures the upper portion of the mount body to the ankle body, wherein the mount body is pivotable about the pin,
   wherein the resilient joint subassembly further comprises opposed first and second spring elements spaced apart relative to the longitudinal axis of the prosthetic foot, wherein each of the first and second spring elements engages one or more inner surfaces of the ankle body, and wherein the lower portion of the mount body is positioned between and engagement with the first and second spring elements.

7. The ankle assembly of claim 1, wherein the endoskeletal connector is a pyramid connector.

8. The ankle assembly of claim 6, wherein the first and second spring elements comprise bumpers.

9. The ankle assembly of claim 1, wherein the ankle body has a continuous, uninterrupted lower surface.

10. The ankle assembly of claim 1, wherein the resilient joint subassembly comprises a mount having:
    a mount body having:
       an upper portion secured to the endoskeletal connector; and
       a lower portion extending downwardly from the upper portion, wherein the lower portion has a forward-facing surface and a rear-facing surface opposite the forward facing surface;
    a pin that secures the upper portion of the mount body to the ankle body so that the mount body is pivotable relative to the ankle body;
    a first spring element that is configured to bias against the forward-facing surface of the mount body to bias the mount body in a first rotational position about the pin; and
    a second spring element that is configured to bias against the rear-facing surface of the mount body to bias the mount body in a second rotational position about the pin opposite the first direction.

11. The ankle assembly of claim 10, wherein the forward-facing surface and the rear-facing surface of the lower portion of the mount body are planar and parallel.

12. The ankle assembly of claim 10, wherein each of the first and second spring elements is a bumper that extends between and contacts each of the lower portion of the mount body and an inner surface of the ankle body.

13. The ankle assembly of claim 12, wherein each of the first and second spring elements is rectangular in cross section.

14. The ankle assembly of claim 1, wherein the taper of the ankle body comprises longitudinally opposed front and rear outer surfaces that converge in a downward direction.

15. A foot-ankle system comprising:
    a prosthetic foot defining a receptacle and having a longitudinal axis and toe and heel portions spaced apart relative to the longitudinal axis; and
    an ankle assembly having:
       a resilient joint subassembly configured for at least partial receipt within the receptacle of the prosthetic foot;
       an endoskeletal connector secured to the resilient joint subassembly and configured for mechanical coupling with a prosthetic leg; and
       an ankle body having inner surfaces that are configured to receive at least a portion of the resilient joint subassembly and outer surfaces that are configured to engage interior surfaces of a receptacle of the prosthetic foot,
    wherein the ankle body has a taper, wherein the receptacle of the prosthetic foot has a sloped or tapered inner surface, wherein the taper of the ankle body and the sloped or tapered inner surface of the receptacle of the prosthetic foot are configured cooperate to define a tapered connection having a posterior aspect that is configured to receive a greatest portion of a tensile stress generated during a late stance phase of walking,
    wherein upon receipt of the resilient joint subassembly within the receptacle of the prosthetic foot, the resilient joint subassembly is configured to permit pivotal movement of the endoskeletal connector from a start position relative to a transverse pivot axis that is perpendicular or oblique to the longitudinal axis of the prosthetic foot, and
    wherein upon pivotal movement of the endoskeletal connector in a forward direction toward the toe portion of the prosthetic foot or in a rearward direction toward the heel portion of the prosthetic foot, the resilient joint subassembly is configured to apply a return force to urge the endoskeletal connector toward the start position.

16. The foot-ankle system of claim 15, wherein the resilient joint subassembly comprises opposed first and second springs spaced apart relative to the longitudinal axis of the prosthetic foot.

17. The foot-ankle system of claim 15, wherein the resilient joint subassembly comprises a mount having:
    a mount body having:
       an upper portion secured to the endoskeletal connector; and
       a lower portion extending downwardly from the upper portion; and
    a pin that secures the upper portion of the mount body to the ankle body, wherein the mount body is pivotable about the pin,
    wherein the resilient joint subassembly further comprises opposed first and second spring elements spaced apart relative to the longitudinal axis of the prosthetic foot, wherein each of the first and second spring elements engages one or more inner surfaces of the ankle body, and wherein the lower portion of the mount body is positioned between and engagement with the first and second spring elements.

18. The foot-ankle system of claim 15, wherein the endoskeletal connector is a pyramid connector.

19. The foot-ankle system of claim 15, wherein interior surfaces of the prosthetic foot define the receptacle of the prosthetic foot, and wherein the resilient joint subassembly of the ankle assembly is shaped to complementarily engage at least a portion of the interior surfaces of the prosthetic foot.

20. The foot-ankle system of claim 19, wherein the prosthetic foot defines an opening through which the ankle assembly is inserted into the receptacle of the prosthetic foot, and wherein the interior surfaces of the prosthetic foot comprise a rear surface that is recessed in a rearward direction relative to the opening of the prosthetic foot.

21. The foot-ankle system of claim 15, wherein interior surfaces of the prosthetic foot define the receptacle of the prosthetic foot, wherein the prosthetic foot further comprises an insert that engages the interior surfaces of the receptacle of the prosthetic foot, and wherein the resilient joint subassembly of the ankle assembly is shaped to complementarily engage at least a portion of the insert of the prosthetic foot.

22. The foot-ankle system of claim 21, wherein the prosthetic foot defines an opening through which the ankle assembly is inserted into the receptacle of the prosthetic foot, and wherein the insert of the prosthetic foot comprises a rear surface that is recessed in a rearward direction relative to the opening of the prosthetic foot.

23. The foot-ankle system of claim 17, wherein the first and second spring elements comprise bumpers.

24. The foot-ankle system of claim 17, wherein portions of the inner walls of the ankle body that contact the first and second spring elements are sloped such that narrowest parts of the wall are closest to the pin and widest parts of the wall are farthest from the pin.

25. The foot-ankle system of claim 24, wherein the portions of the inner walls of the ankle body that contact the first and second spring elements are sloped at an angle ranging from 2 degrees to 10 degrees.

26. The foot-ankle system of claim 17, wherein the prosthetic foot defines a bore extending between an exterior surface of the prosthetic foot and the receptacle of the prosthetic foot, wherein the foot-ankle system further comprises a fastener that is received within the bore to selectively secure the ankle assembly within the receptacle of the prosthetic foot.

27. The foot-ankle system of claim 17, wherein the receptacle of the prosthetic foot has a sloped or tapered inner surface that is configured to guide the ankle body into the receptacle of the prosthetic foot.

28. The foot-ankle system of claim 17, wherein the interior surfaces of the receptacle of the prosthetic foot comprise a rear surface that is recessed in a rearward direction.

29. The foot-ankle system of claim 28, wherein the interior surfaces of the receptacle of the prosthetic foot further comprise a front surface that is recessed in a forward direction.

30. The foot-ankle system of claim 29, wherein the front and rear surfaces of the receptacle of the prosthetic foot define respective slots or grooves for receiving a complementary portion of the ankle body to thereby secure the resilient joint assembly within the receptacle.

31. A method comprising:
using a foot-ankle system comprising:
a prosthetic foot defining a receptacle and having a longitudinal axis and toe and heel portions spaced apart relative to the longitudinal axis; and
an ankle assembly having:
a resilient joint subassembly configured for at least partial receipt within the receptacle of the prosthetic foot;
an endoskeletal connector secured to the resilient joint subassembly and configured for mechanical coupling with a prosthetic leg; and
an ankle body having inner surfaces that are configured to receive at least a portion of the resilient joint subassembly and outer surfaces that are configured to engage interior surfaces of a receptacle of the prosthetic foot;
wherein the ankle body has a taper, wherein the receptacle of the prosthetic foot has a sloped or tapered inner surface, wherein the taper of the ankle body and the sloped or tapered inner surface of the receptacle of the prosthetic foot cooperate to define a tapered connection having a posterior aspect that is configured to receive a greatest portion of a tensile stress generated during a late stance phase of walking,
inserting at least a portion of the resilient joint subassembly of the ankle assembly within the receptacle of the prosthetic foot; and
mechanically coupling the ankle assembly to the prosthetic foot,
wherein upon receipt of the resilient joint subassembly within the receptacle of the prosthetic foot, the resilient joint subassembly is configured to permit pivotal movement of the endoskeletal connector from a start position relative to a transverse pivot axis that is perpendicular or oblique to the longitudinal axis of the prosthetic foot, and
wherein upon pivotal movement of the endoskeletal connector in a forward direction toward the toe portion of the prosthetic foot or in a rearward direction toward the heel portion of the prosthetic foot, the resilient joint subassembly is configured to apply a return force to urge the endoskeletal connector toward the start position.

32. The method of claim 31, wherein the endoskeletal connector of the ankle assembly is mechanically coupled to a prosthetic leg.

33. The method of claim 31, wherein the prosthetic foot is positioned within a shoe before the ankle assembly is coupled to the prosthetic foot.

34. The method of claim 31, further comprising:
decoupling the ankle assembly from the prosthetic foot; and
removing the resilient joint assembly from the receptacle of the prosthetic foot.

35. The method of claim 34, wherein the prosthetic foot is a first prosthetic foot, the method further comprising:
inserting at least a portion of the resilient joint subassembly of the ankle assembly within the receptacle of a second prosthetic foot; and
mechanically coupling the ankle assembly to the second prosthetic foot.

36. The method of claim 35, wherein the second prosthetic foot has a different shape than the first prosthetic foot.

37. The method of claim 35, wherein the second prosthetic foot is positioned within a shoe before the ankle assembly is coupled to the second prosthetic foot.

* * * * *